US012725688B2

(12) United States Patent
Stephens

(10) Patent No.: US 12,725,688 B2
(45) Date of Patent: Sep. 1, 2026

(54) USING MACHINE LEARNING TO PREDICT CELL THERAPY CHARACTERISTICS

(71) Applicant: AiCella, Inc., San Diego, CA (US)

(72) Inventor: Geoffrey Stephens, San Diego, CA (US)

(73) Assignee: AiCella, Inc., San Diego, CA (US)

( * ) Notice: Subject to any disclaimer, the term of this patent is extended or adjusted under 35 U.S.C. 154(b) by 46 days.

(21) Appl. No.: 18/633,930

(22) Filed: Apr. 12, 2024

(65) Prior Publication Data

US 2025/0322924 A1 Oct. 16, 2025

(51) Int. Cl.

| | |
|---|---|
| ***G16H 20/00*** | (2018.01) |
| ***G16B 40/00*** | (2019.01) |
| ***G16H 70/40*** | (2018.01) |

(52) U.S. Cl.

CPC ............. *G16H 20/00* (2018.01); *G16B 40/00* (2019.02); *G16H 70/40* (2018.01)

(58) Field of Classification Search

CPC ......... G16H 20/00; G16H 70/40; G16B 40/00
See application file for complete search history.

(56) References Cited

U.S. PATENT DOCUMENTS 4,338,635 A * 7/1982 Haider ................... H04N 5/655 348/836
12,268,207 B2 * 4/2025 Woods ................... A01N 1/162
2016/0150081 A1 * 5/2016 Shivashankaraiah ... H04M 3/44 455/564
2020/0258633 A1 8/2020 Webb et al.
2021/0133592 A1 5/2021 Schillebeeckx et al.
2021/0195888 A1 * 7/2021 Muniz Ferreira .... C12N 5/0664
2021/0297470 A1 * 9/2021 Goodman ............... G06F 16/64
2021/0366577 A1 * 11/2021 Koller .................... G06N 3/045

(Continued)

FOREIGN PATENT DOCUMENTS

WO WO-2024097314 A2 * 5/2024 ......... A61K 40/4211
WO WO-2024158900 A1 * 8/2024 ............. G16H 10/20

OTHER PUBLICATIONS

WO: International Search Report and Written Opinion in International (PCT) Application No. PCT/2025/024060 dated Jun. 24, 2025 (16 pages).

*Primary Examiner* — Kambiz Abdi
*Assistant Examiner* — Sheryl G Patel
(74) *Attorney, Agent, or Firm* — Snell & Wilmer, L.L.P.

(57) ABSTRACT

Disclosed are systems and methods for improving processes for developing cell therapies by applying machine learning to data including manufacturing process data and clinical measurements (e.g., patient response and treatment data) to determine parameters and settings for a manufacturing process for engineering cells for use in cell therapy. Parameters and settings for a manufacturing process for genetically engineered T-cells including, but not limited to, Chimeric Antigen Receptor (CAR) T cells can be determined. A method can include receiving a set of process parameters of a cell engineering process, predicting a clinical response associated with an output of the cell engineering process by applying a machine learning model on the received set of process parameters, where the machine learning model is trained on process parameter data and clinical response data, and generating a visualization for use in a graphical user interface of the predicted clinical response.

9 Claims, 34 Drawing Sheets

(56) References Cited

U.S. PATENT DOCUMENTS

| | | | | |
|---|---|---|---|---|
| 2021/0388389 | A1 | 12/2021 | Chen et al. | |
| 2022/0380717 | A1 * | 12/2022 | Terao | C12N 5/00 |
| 2023/0178239 | A1 | 6/2023 | Hause et al. | |
| 2024/0071256 | A1 * | 2/2024 | Craig | G09B 23/30 |

* cited by examiner

Convolutional Neural Network 420

Initial Input

Convolved Output

Subsampled Convolved Output

Convolved Output

Convolved Output

F1 F2 F3 FN

First Convolution Layer 422

Subsampling Layer 428

Second Convolution Layer 424

Convolution Layer 426

Fully Connected Layer 430

600

| response | patient id | PH | D0_Via | pO2_d1 | pO2_d2 | pO2_d3 |
|---|---|---|---|---|---|---|
| 1.00 | U | 1.00 | 0.54 | 0.17 | 1.20 | 0.23 |
| 1.00 | U.3 | 1.00 | 0.74 | 0.77 | 4.81 | 0.83 |
| 0.00 | U.6 | 0.00 | 0.34 | 0.37 | 2.43 | 0.43 |
| 1.00 | U.7 | 0.00 | 0.22 | 0.91 | 5.36 | 0.97 |
| 1.00 | U.16 | 0.00 | 0.63 | 0.71 | 4.45 | 0.77 |
| 0.00 | U.19 | 1.00 | 0.27 | 0.32 | 2.07 | 0.35 |
| 1.00 | U.25 | 1.00 | 0.49 | 0.52 | 3.29 | 0.55 |
| 0.00 | U.29 | 0.00 | 0.63 | 0.55 | 4.11 | 0.71 |
| 0.00 | U.31 | 1.00 | 0.69 | 0.72 | 4.52 | 0.73 |
| 0.00 | U.32 | 0.00 | 0.23 | 0.26 | 1.72 | 0.32 |
| 0.00 | U.34 | 1.00 | 0.30 | 0.32 | 2.53 | 0.38 |
| 0.00 | U.41 | 1.00 | 0.03 | 0.06 | 0.55 | 0.12 |

Model Performance

| pO2_d4 | pH_d1 | p |
|---|---|---|
| 0.26 | 35.63 | 221 |
| 0.85 | 309.65 | 64 |
| 0.45 | 60.67 | 36 |
| 1.00 | 135 | 31 |
| 0.80 | 302.41 | 600 |
| 0.40 | 53.44 | 324 |
| 0.61 | 78.43 | 451 |
| 0.74 | 75.15 | 567 |
| 0.21 | 503.53 | 601 |
| 0.35 | 46.20 | 208 |
| 0.41 | 54.55 | 333 |
| 0.15 | 22.27 | 542 |

Prediction Inspector - Test Set

| patient id | measured | predicted |
|---|---|---|
| U | 1 | 0.88 |
| U.3 | 1 | 0.88 |
| U.6 | 0 | 0.88 |
| U.7 | 1 | 0.88 |
| U.16 | 0 | 0.55 |
| U.41 | 0 | 0.12 |
| U.44 | 0 | 0.12 |
| U.57 | 0 | 0.12 |
| U.64 | 0 | 0.88 |
| U.67 | 1 | 0.88 |
| U.71 | 1 | 0.88 |
| U.92 | 1 | 0.12 |

Input▾ Analysis Data Portal Optimization Help▾

AiCella Inc

PCA SHAP Exploration Data Inspector

Source Data

Show 10 entries

| | response | patient_id | pH...3 | D0_Via | pO2_d1 |
|---|---|---|---|---|---|
| 1 | 1 | U | 1 | 3305.053486 | 115308.0044 |
| 2 | 1 | U.3 | 1 | 878.4632434 | 23095.67787 |
| 3 | 1 | U.6 | 0 | 5309.670409 | 3898.949656 |
| 4 | 1 | U.7 | 0 | 864.3617021 | 65824.46809 |
| 5 | 1 | U.16 | 0 | 1520.12957 | 72327.6261 |
| 6 | 1 | U.19 | 1 | 1501.774623 | 69343.38953 |
| 7 | 1 | U.25 | 1 | 1683.311141 | 34687.08389 |
| 8 | 1 | U.29 | 0 | 348.9503121 | 12669.20645 |

661

Search:

| pO2_d2 | pO2_d3 | pO2_d4 |
|---|---|---|
| 67746.21911 | 276163.7772 | 466543.710 |
| 9886.220909 | 123369.0432 | 87192.4639 |
| 29293.73415 | 68880.84028 | 89020.2825 |
| 20414.89362 | 72077.12766 | 196726.063 |
| 22711.70754 | 372880.6108 | 265747.339 |
| 21823.42502 | 322553.2387 | 268795.474 |
| 15450.51043 | 185286.285 | 140346.205 |
| 3908.973008 | 18863.98638 | 51260.4360 |

Model Performance | Model Stats | Prediction Table

ROC Stats

Show 25 entries Search:

| Statistic | Frequency |
|---|---|
| Sensitivity | 1 |
| Specificity | 0.947 |
| Pos Pred Value | 0.75 |
| Neg Pred Value | 1 |
| Precision | 0.75 |
| Recall | 1 |
| F1 | 0.857 |
| Prevalence | 0.136 |
| Detection Rate | 0.136 |
| Detection Prevalence | 0.182 |
| Balanced Accuracy | 0.974 |

Statistic Frequency

Showing 1 to 11 of 11 entries Previous 1 Next

665

Model Performance | Model Stats | Prediction Table

Prediction Inspector - Test Set

Show 25 entries Search:

| PatientID | measured | predicted |
|---|---|---|
| U.19 | 1 | 1.000064850 |
| U.25 | 1 | 1.000367522 |
| U.53 | 1 | 1.003902555 |
| U.59 | 1 | 1.000045776 |
| U.67 | 1 | 0.999938905 |
| U.72 | 1 | 0.968375862 |
| U.81 | 1 | 1.000114918 |
| U.105 | 1 | 0.986326396 |
| U.117 | 1 | 0.190422177 |
| U.122 | 1 | 0.995164990 |
| U.148 | 1 | 0.999197900 |
| U.230 | 1 | 0.999938905 |
| U.256 | 1 | 1.000045776 |
| U.257 | 1 | 1.000114918 |
| U.266 | 1 | 1.000633597 |
| U.278 | 1 | 0.999886751 |
| U.291 | 1 | 1.000367522 |
| U.292 | 1 | 0.989155650 |

FIG. 6G

USING MACHINE LEARNING TO PREDICT CELL THERAPY CHARACTERISTICS

TECHNICAL FIELD

Disclosed are systems and methods for improving processes for developing cell therapies using machine learning.

BACKGROUND

Cell therapy provides great promise in the treatment of illness such as cancer, infectious disease, organ transplantation, and autoimmune conditions. However, the process of manufacturing cells for use in cell therapy remains a highly variable and subjective process. For example, the production of cell therapies is intensive and requires extensive resources. Often manufacturing runs are unable to produce successful cells, and even when cells are produced by the manufacturing process appear to be successful, the successful production of cells does not guarantee a positive patient outcome.

SUMMARY

Disclosed are systems and methods for improving processes for developing cell therapies using machine learning.

In one aspect, a method includes the steps of: receiving, by at least one processor, a set of process parameters of a cell engineering process, predicting, by the at least one processor, a clinical response associated with an output of the cell engineering process by applying a machine learning model to the received set of process parameters, where the machine learning model is trained on process parameter data and clinical response data, and generating, by the at least one processor, data usable to generate a visualization in a graphical user interface of the predicted clinical response.

Optionally, implementations can include one or a combination of two or more of the following features. The set of process parameters can include at least one of: operator identification, initial volume, donor, mixing, dilution speed, input bag rinsing, optical cell detection, product filing speed, waste extraction speed, intermediate volume, pre-wash cycles, pre-wash g-force, pre-wash sedimentation time, switch washing solution, lactate concentration, oxygen concentration, $CO_2$ concentration, hold time prior to freeze, cell freezing parameters, and thaw parameters.

The machine learning model can include at least one of logistic regression, an elastic net, a k-nearest neighbor, a decision tree, a random forest, a support vector machine, a support vector, a light gradient boosting method, an extreme gradient boosting method, a neural network, or a multi-layer perceptron. The clinical response data can include at least one of patient outcomes data, or patient demographic data. The process parameter data can include operator identification, initial volume, donor, mixing, dilution speed, input bag rinsing, optical cell detection, product filing speed, waste extraction speed, intermediate volume, pre-wash cycles, pre-wash g-force, pre-wash sedimentation time, switch washing solution, lactate concentration, oxygen concentration, $CO_2$ concentration, hold time prior to freeze, cell freezing parameters, and thaw parameters. The machine learning model can be trained on in vitro assay results of the cell engineering process, wherein the in vitro assay results including one or more of a cell number, percentage phenotype, cell recovery data, cell diameter, hold time, expansion properties of the engineered cells, persistence properties of the engineered cells, cytokine release patterns, or cytotoxicity levels in vitro. Optionally, the cell engineering process includes a process for generating Chimeric Antigen Receptor (CAR) T cells.

The process can include pre-processing the received set of process parameters by at least one of cleaning, deduplicating, standardizing, transforming, applying feature engineering, normalizing, scaling, encoding, integrating, or reducing the received set of process parameters. One or more process parameters of the cell engineering process can be adjusted based on the predicted clinical response. A set of cells can be generated based on the cell engineering process having adjusted process parameters. Providing the predicted clinical response can include displaying in a graphical user interface the predicted clinical response and at least one of: one or more characteristics of the trained machine learning model, or the received set of process parameters.

In one aspect, a method includes the steps of: receiving, by the at least one processor, a clinical data set comprising patient outcomes from applying a cell therapy product to one or more patients of the clinical data set, receiving, by the at least one processor, a process data set comprising one or more process parameters associated with generating the cell therapy product, training, by the at least one processor, a machine learning model to identify one or more process parameters associated with a positive patient outcome based on the received clinical data set and the received process data set, and providing, by the at least one processor, the trained machine learning model for use in predicting a clinical response.

Optionally, implementations can include one or a combination of two or more of the following features. The machine learning model can include at least one of logistic regression, an elastic net, a k-nearest neighbor, a decision tree, a random forest, a support vector machine, a support vector, a light gradient boosting method, an extreme gradient boosting method, or a multi-layer perceptron. The clinical data set includes at least one of: patient outcomes data, or patient demographic data. The process data set includes at least one of: operator identification, initial volume, donor, mixing, dilution speed, input bag rinsing, optical cell detection, product filing speed, waste extraction speed, intermediate volume, pre-wash cycles, pre-wash g-force, pre-wash sedimentation time, switch washing solution, lactate concentration, oxygen concentration, $CO_2$ concentration, hold time prior to freeze, cell freezing parameters, and thaw parameters. The cell therapy product includes Chimeric Antigen Receptor (CAR) T cells. Training the machine learning model can include training on in vitro assay results of the cell engineering process, where the in vitro assay results include one or more of a cell number, percentage phenotype, cell recovery data, cell diameter, hold time, expansion properties of the engineered cells, persistence properties of the engineered cells, cytokine release patterns, or cytotoxicity levels in vitro. Generating a synthetic training data set can include applying at least one of a generative adversarial network and a transfer learning process to the clinical data set and process data set. The trained machine learning model is applied to a set of process parameters to identify at least a set of process parameters that can be improved.

In an aspect, a system including one or more processors and a memory storage in data communication with the one or more processors, can have the memory storage storing instructions executable by the one or more processors and that upon such execution cause the one or more processors to perform operations of: receiving a set of process parameters of a cell engineering process, predicting a clinical response associated with an output of the cell engineering process by applying a machine learning model to the received set of process parameters, where the machine learning model is trained on process parameter data and clinical response data, and generating data usable to generate a visualization in a graphical user interface of the predicted clinical response.

In another aspect, a non-transitory computer storage medium encoded with a computer program, can include program comprising instructions that when executed by data processing apparatus cause the data processing apparatus to perform operations of: receiving a set of process parameters of a cell engineering process, predicting a clinical response associated with an output of the cell engineering process by applying a machine learning model to the received set of process parameters, where the machine learning model is trained on process parameter data and clinical response data, and generating data usable to generate a visualization in a graphical user interface of the predicted clinical response.

In another aspect, a method can include the steps of receiving, by at least one processor, a set of process parameters of a cell engineering process, receiving, by the at least one processor, a clinical response associated with an output of the cell engineering process derived by applying a machine learning model to the received set of process parameters, where the machine learning model is trained on process parameter data and clinical response data, and displaying, by the at least one processor, the received clinical response in a graphical user interface.

BRIEF DESCRIPTION OF THE DRAWINGS

For a more complete understanding of the present disclosure, reference is now made to the following descriptions taken in conjunction with the accompanying drawing, in which:

FIG. 6G is an illustration of a graphical user interface in accordance with some embodiments of the present disclosure;

DETAILED DESCRIPTION

Figure 1:
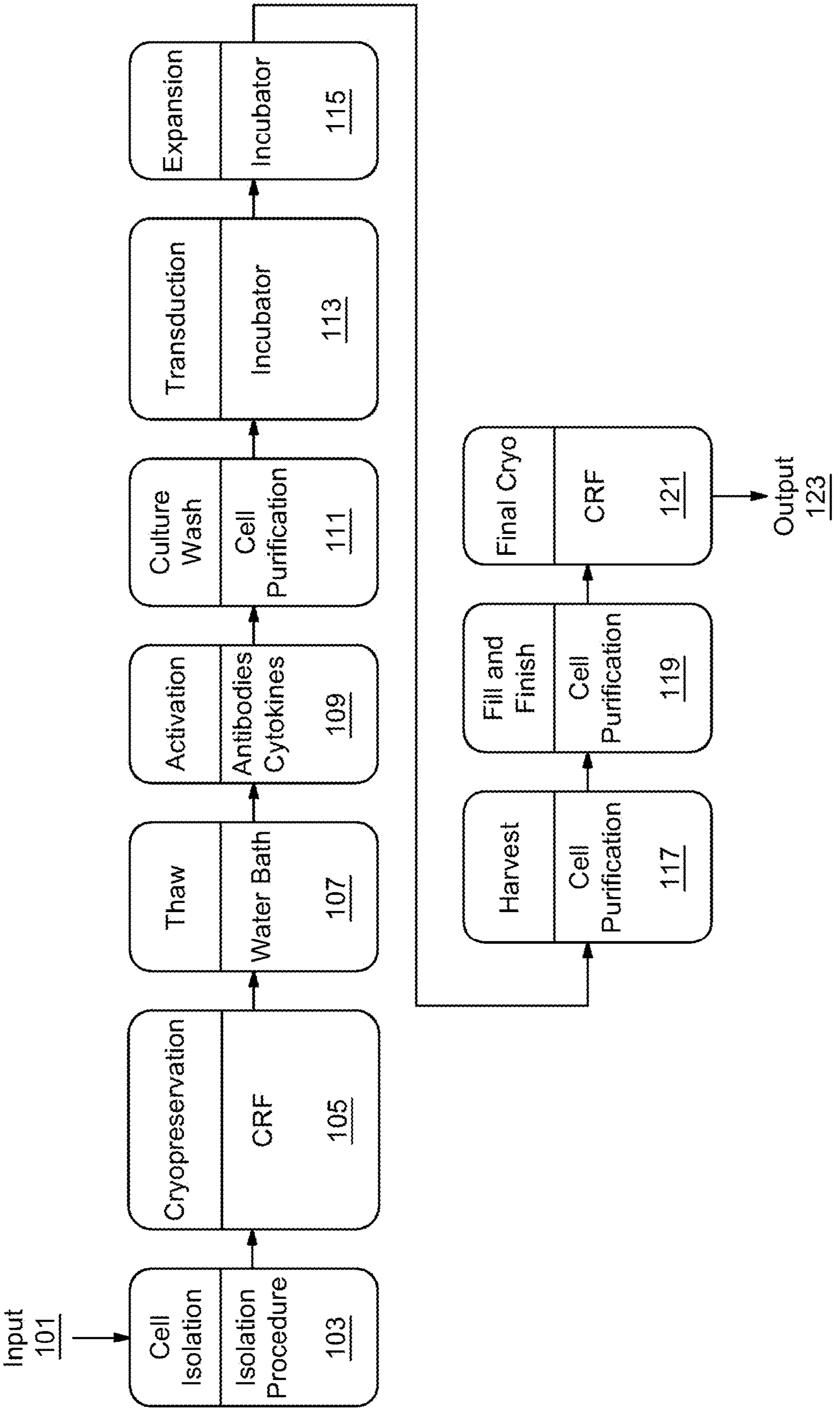
FIG. 1 is a flow-chart illustrating a process development workflow and process development parameters in accordance with some embodiments of the present disclosure.

Systems and methods for improving process for developing cell therapies are disclosed herein. Processes for developing cell therapies can be improved or optimized by applying machine learning to data including manufacturing process data and clinical measurements (e.g., patient response and treatment data). The machine learning approaches can be used to determine improved or optimal parameters and settings for a manufacturing process that can be used for engineering cells for use in cell therapy. For example, the disclosed systems and methods are used to determine improved and/or optimal parameters and settings for a manufacturing process for genetically engineered T-cells including, but not limited to, Chimeric Antigen Receptor (CAR) T cells.

Genetically engineered T-cells, and more specifically, Chimeric Antigen Receptor (CAR) T cells, hold promise as a cancer therapy for patients who may have failed other therapy treatments. However, the production of genetically engineered T-cells is highly intricate and resource-intensive. The complex manufacturing processes for producing or generating genetically engineered T-cells can produce variable numbers of T-cells or T-cells with poor quality. Accordingly, often patients do not respond well to these genetically engineered T-cells, which may be due in part to the poor quality of the cells produced by existing processes. Thus, there remains a need to identify parameters and process techniques that may result in the production of the genetically engineered T-cells with improved quality at improved quantities. Identification of specific parameters of cell products and process procedures and parameters that may result in improved patient responses may lead to improved production of engineered T-cells.

Various machine learning techniques can be applied to manufacturing process data and clinical measurements to predict patient response to a genetically engineered cell that is manufactured according to a set of manufacturing parameters. In some embodiments, the disclosed systems and methods are used to identify manufacturing parameters and/or cell products mostly likely to impact patient response to a cell engineered using the manufacturing process and are used to optimize or improve a manufacturing process for engineering cells. In some embodiments, the disclosed systems and methods provide data visualizations to a user that show the impact of particular parameters related to the manufacturing process or cell products on clinical results such as patient response. For example, a visualization tool can present a plurality of artificial intelligence and machine learning based algorithms in a user-friendly interface that allows users to view how changes to process parameters can potentially impact patient responses. The visualization tool can also be configured to perform simulations. Simulations could allow for estimations as to how changes in process parameters can impact the produced T-cells and/or patient outcomes. The visualization tool can be provided in an application, web-application, or the like. Visualization tools can be provided to enable non-data scientists to manipulate data, and view impacts on process parameters that may impact cell quality and quantity as well as patient response easily, without the need for specialized advanced computer skills.

Although processes for genetically engineered T-cells are described herein, it is envisioned that the described systems and methods can be used in connection with any complex cell development process. For example, the disclosed systems and methods can be used in connection with processes for manufacturing embryonic stem cells, mesenchymal stem cells, pluripotent stem cells, and the like. Engineered cell therapies can be used in the treatment of cancer, hematological malignancies, and/or autoimmune diseases.

Systems and methods for improving or optimizing processes for developing cell therapies by applying artificial intelligence and/or machine learning to data including manufacturing process data and clinical measurements (e.g., patient response and treatment data) are discussed herein. Machine learning based systems can involve the use of computer-implemented methods, devices, systems and computer-readable media. Machine learning can refer to a process within artificial intelligence that includes the training of software to analyze statistical information about data provided to the software such that it can learn from the provided data and generalize to unseen data. Accordingly, a trained machine learning software is capable of providing predictions on unseen data. Thus, a machine learning software can undergo a first training phase, where it is trained using training data. Afterwards, the machine learning software can be applied to new data in a second application phase.

Training data for the artificial intelligence models described herein can include process development data corresponding to a process for engineering cells. FIG. 1 illustrates a process for engineering cells. The process involved in generating living "drugs" such as engineered cells like CAR-T cells is highly complex in nature requiring multiple unit operations, representing distinct pieces of equipment or manipulations, which are employed over the course of the CAR-T development process. The parameters associated with the complex process for generating engineered cells can be included in process development data.

As illustrated in FIG. 1 a process 100 for engineering cells may take in as input 101 and perform the following steps: cell isolation 103, cryopreservation 105, thaw 107, activation 109, culture wash 111, transduction 113, expansion 115, harvest 117, fill and finish 119, and a final cyropreservation 121 in order to generate output 123 including CAR T-cells. Input 101 can include biological materials such as patient material. In some embodiments patient material can be derived from a leukapheresis collection or from patient whole blood.

In a first step of the process 100 cells can be isolated 103. Blood products are first collected from a human subject by venipuncture followed by leukapheresis into collection bags or by collection in standard evacuated blood containers (e.g. Becton Dickinson Vacutainers). The mononuclear cells (i.e., lymphocytes) may be subsequently isolated by centrifugation of blood products overlayed on density gradients such as Ficoll or Lymphoprep™, or similar. Subsets of lymphocytes (T cells, NK cell, B cells) may be further isolated using antibody-coupled ferrous beads with magnetic columns, size exclusion columns, limiting dilution, or by fluorescence activated cell sorting (FACS).

A second step of the process can include cryopreservation 105. Cryopreservation 105 involves the use of cell suspensions that are frozen either following collection from a patient or after the harvest of a cell product intended for treatment of a patient. The cells are frozen in special freezing media such as, but not limited to, Cryostore-10 (CS10), Cryostore-5 (CS5), or culture media containing 5%-105 dimethyl sulfoxide (DMSO) to facilitate the survival of the cells throughout the freezing and storage process in liquid or vapor phase $N_2$. The process of freezing is facilitated using controlled rate freezers or other devices such as the Corning CoolCell™ that permit the freezing process to occur in a well-controlled manner.

After the cells are cryopreserved, they undergo a thawing process 107.

The process of thawing 107 the cells after cryopreservation 105 is a critical step in the reconstitution of cellular function after storage. The frozen vials of cells are rapidly thawed by hand or using an automated device like a Cytiva VIA Thaw™ dry automated thawers. Once thawed, the suspension is transferred to a tube where pre-warmed culture media is slowly added, drop by drop, to minimize osmotic shock. The cells are then washed in culture media and then placed into appropriate culture bags or flasks where they are allowed to recover.

After thawing, cell products can go through an activation process 109. The process of lymphocyte activation allows for many downstream manipulations (i.e., genetic engineering) and for the expansion of cells prior to reinfusion back into the patient. Activation 109 can be achieved by one of several techniques, including but not limited to, culturing lymphocytes on plates coated to a with CD3- and CD28-specific antibodies in stationary phase, beads coated with the same, activating agents like phorbol 12-myristate 13-acetate plus ionomycin, concanavalin A (ConA), or peptide/MHC complexes either expressed on the surface of antigen presenting cells or in stationary phase.

After the cell products are activated, they can undergo a culture wash 111. During a culture wash 111, spent culture medium is removed from cells and replaced with a fresh supply of medium to remove waste products and provide nutrients to promote cells growth. The wash can be achieved by centrifugation of cells and removal of media via decanting or aspiration of the supernatant and can occur either using automated equipment like a Sepax or Lovo or similar, or manually.

In a next step of process 100 the cell products can undergo transduction 113. During transduction 113 genetic material is transferred from one cell to another using a virus as a vector. It is used in gene therapy applications, where viruses are engineered to carry specific genes into target cells for various purposes, such as gene delivery or genetic modification. For example, lenti- or retro-viral particles are often used carriers or “vectors” that are added into the cell culture medium where they cross the cytoplasmic membrane after binding to cell surface receptors and then transfer the genetic information of interest to the target cells.

Cell expansion 115 occurs after transduction and involves culturing activated cells in culture media containing combinations of growth factors, including but not limited to IL-2, IL-7, and IL-15, which are commonly used. Cell expansion 115 results in an increase in the cell number so as to meet the required dosage for the patient.

Once a sufficient number of cells has be reached to achieve the target dosage for the patient, the cells are collected from their expansion container(s) and subjected to a culture wash regime in a harvesting step 117. The washed cells are collected and resuspended in a culture media formulation containing the requisite amount of cryomedium for the fill and process.

After the formulated cells are harvested in step 117, they undergo a fill and finish step 119. In this step, the formulated cells are filled into appropriate containers for storage and transportation. These containers may include cryovials, bags, or other types of sterile packaging, depending on the specific requirements of the therapy and the route of administration. Once filled, the containers are sealed and labeled with relevant information, such as patient identifiers, lot numbers, and expiration dates. This step ensures traceability and compliance with regulatory requirements.

The last step of a process 100 includes a final cryopreservation 121 step. During this step, the cell suspension is cryopreserved for future use in the patient using techniques analogous to those discussed in the cryopreservation step 105.

The output 123 of the process 100 includes engineered cells and cell products.

Training data for the artificial intelligence models described herein can include process development data, clinical outcomes data and cell product data. One or more process development parameters can be associated with each of the steps of cell isolation 103, cryopreservation 105, thaw 107, activation 109, culture wash 111, transduction 113, expansion 115, harvest 117, fill and finish 119, and a final cryopreservation 121 illustrated in FIG. 1.

The process development data can be paired with corresponding clinical outcomes data. Process development parameters can correspond to values and settings for specialized equipment used in the engineering of cells. In some embodiments, process development data and parameters include timings, flow cytometry settings, pre- and post-peripheral blood mononuclear cells (PMBC) isolation data, culture initiation, in process measurements, harvest data, freezing data, post thaw data, infusion data, and patient outcomes.

For example, timing data included in the process development data can include data related to the activation and stimuli used (days), transduction day, initiation of expansion (day), cytokines added (type, timing, frequency).

Flow cytometry data included in the process development data can include CD Markers (%) (e.g., CD3, CD4, CD8, CD25, CD45, CD45RA/RO), percentage of CAR expression, T cell memory, T cell exhaustion markers (PD1, TIM3, LAG3, etc.), T cell homing (CXCR3, CCR2, CCR7, CCR5, etc.), Non-T cells (e.g., CD14, CD19, CD56), treg markers (FoxP3, Helios, IL10), and the like.

Pre- and post-PBMC isolation data included in process development data can include data obtained from whole blood, including, but not limited to, the total cells, viability of cells, and estimated recovery.

Process development data can include data indicative of culture initiation such as the total cells seeded, cell density, and culture medium used.

Process development data can also include in-process measurements. The in-process measurements can be obtained at one or more time points between day 0 to harvest of the cells. These in-process measurements can include a measure of the total cells, viability of cells (e.g., expressed as a percentage), and/or days of media change.

Harvest data can also be included in the process development data. Harvest data can be obtained post or pre-release and include one or more of the number of total cells produced, total T cells produced, total CAR-T cells produced, percentages of CD3+, CAR+, percentages of T cell subsets including CD3 and CD4+, and CD3 and CD8+, percentages for CD4 and CAR+, and CD8 and CAR+, and the percentage viability.

Freezing data can also include time from harvest to freeze, freezing parameters and media used, freezing techniques used, and the like.

Post-thaw data can include identity of the cells (e.g., HLA data), potency of the cells (tumor cell killing, EBV specificity, CAR expression), transgene expression (flow and transgene copy number per cell), and PCR data.

Infusion data can include one or more of time from thaw to infusion, the total cells, viability percentage, CAR+ cell percentage, cells, and viral copy number (VCN).

Additional specialized equipment can include, but is not limited to, cold storages, biosafety cabinets and carbon dioxide incubators, fume hoods, analytical balances, precision balances, pH meters, microscopes (i.e., inverted, fluorescent, compound, stereo), cell counters, PCR machines, thermal cyclers, flow cytometers, laminar flow hoods, incubators, centrifuges, HPLC, FPLC, spectrophotometers, flurometers, orbital shakers, vacuum pumps, water baths, electroporators, gel electrophoresis, blog and gel imagers, multimode plate readers and plate washers, benchtop SPR, liquid handling, tissue homogenizers, automated sample processors, autoclaves that the like. Accordingly, process development data can include settings and parameters for this specialized equipment.

Clinical outcomes data can be obtained from observations of clinical outcomes associated with the cell products generated based on the respective process development parameters. Training data can include diverse data sources including in vitro assay results, patient characteristics, and treatment outcomes. For example, training data can include data from clinical trials and real-world evidence where in vitro efficacy is measured alongside patient responses. For example, training data can include one or more files with a binary “response” variable that indicates clinical outcomes in the form of response or no response.

In some embodiments, clinical outcomes data includes patient outcome data. This may response data expressed as overall response (OR), complete response (CR), objective clinical response (OCR), no response (NR) or the like. Patient outcomes data can also include ELISpot for EBV and non-viral tumor antigens, and PCR for transgene in blood and tumor.

Cell product data can include data and information about the cell products produced by the development process. For example, training data can include data from in silico analysis of process development parameters. The cell product data can be paired with clinical measurements and/or process development data for use by a machine learning model. For example, the training data can include the expansion and persistence of CAR-T cells, cytokine release patterns, cytotoxicity levels (in vitro) and related patient responses. For example, the cell product data can include data from in vitro studies of the CAR T-cells generated by a process. The data from the in vitro studies can include data indicating cytokine secretion (e.g., TNF-$\alpha$ and IFN-$\gamma$), cytotoxicity assays, proliferation assays, CD4/CD8 ratios, CAR expression, and in vitro serial killing assays.

For example, historical process development and clinical data from CAR-T clinical studies for multiple trials can be used to train one or more machine learning based models.

Training data, such as process development data, clinical outcomes data and cell product data can be obtained from a database. Alternatively, or additionally, the data can be obtained from one or more sensors configured to record or measure the data. For example, one or more temperature sensors, humidity sensors, and the like can provide process development data. In another example, data from electronic health records, CT scans, etc. can be stored in a database, from which the training data is retrieved. To facilitate downstream artificial intelligence based analysis, data formats, units, and metadata can be standardized to ensure consistency across time, sample IDs, and conditions. Standardization can include the application of standard scripting techniques in Python or R to merge and extract features from the exported data.

In some embodiments, scripting languages (i.e., python, R) are used to process data exported from process manufacturing and/or clinical software and databases. For example, data from process manufacturers and/or clinical databases can be merged, have features extracted, and parameters analyzed. Data can also be standardized and transformed into a common format for use by a machine learning model. For example, hand-written batch record data for cell engineering processes can be converted into standardized formats. Clinical outcomes can be used as classifiers for the training data. Further, non-clinical outcomes such as cell yield, CAR-T expression and in vitro potency can also be included in the training data.

Historical data for cell-engineering processes are conventionally stored in a mix of handwritten records, spreadsheets, and other data files in a decentralized, unorganized manner, that prevents process engineers from being able to analyze the impact of process parameters on products. Accordingly, the databases may provide a centralized, regulated, and standardized means of sharing data from cell engineering processes. The disclosed centralized database that leverages storage in a structured SQL data base, the platform will enable efficient utilization of vast amounts of data that were previously underutilized or not fully analyzed. This optimization of data analysis can reveal patterns, correlations, and insights that were previously inaccessible, potentially expediting the development and refinement of cell therapies.

In process development, data regarding process parameters is often recorded in hand-written batch records in laboratory notebooks. In some embodiments, a generative AI model is used to extract and convert the hand-written information into a dataset for use with the systems and methods described herein.

For example, a generative AI model for generating a dataset based on hand-written notes can include specialized neural networks that have been adapted for handwriting by processing images of handwritten text and outputting the recognized characters are used for this purpose. This can include convolutional neural networks (CNNs) and long short-term memory networks (LSTMs). CNN architectures can be adapted for handwriting recognition tasks by processing images of handwritten text and outputting the recognized characters. LSTM architectures can include recurrent neural networks trained on handwritten text. They can capture long-range dependencies in sequential data, making them effective for recognizing handwriting patterns.

Training data may include sensitive clinical and non-clinical patient data and process information. Accordingly, the database may include data protection methods such as encryption, access controls, and compliance measures.

Figure 2A:
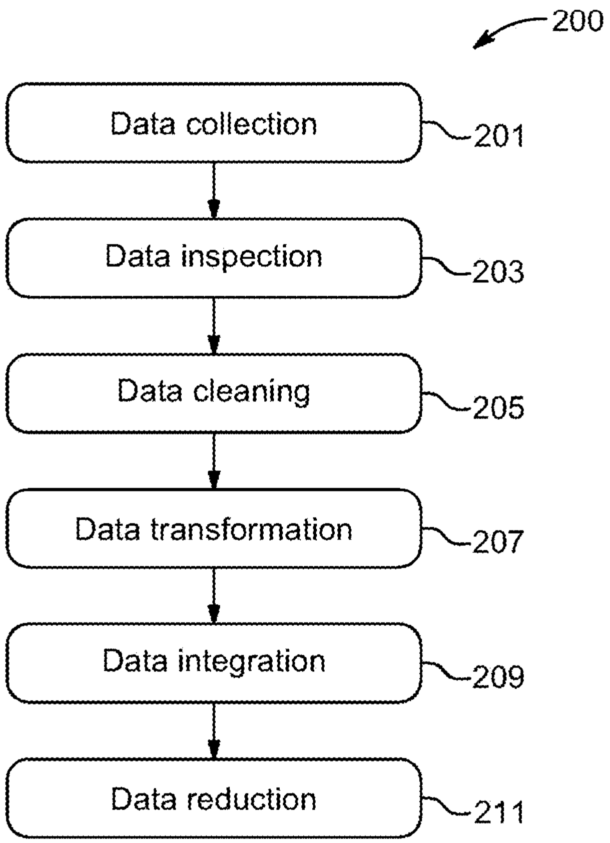
FIG. 2A is a flow-chart illustrating data processing in accordance with some embodiments of the present disclosure.

FIG. 2A illustrates a process 200 for developing training data (and cleaning data for application of the machine learning models described herein.) Developing training data can include the steps of data collection 201, data inspection 203, and data cleaning 205. For example, data collection can include gathering raw data from a plurality of sources such as databases, spreadsheets, applications, or repositories. Data inspection can include understanding the structure and quality of the data and include identifying missing values, inconsistencies, outliers and data types. Data cleaning can include the handling of missing or erroneous data. For example, this may include imputing missing values, removing values, or interpolating between values. Data cleaning can also include identifying and processing duplicate records. Data cleaning can also include standardizing data formats.

After the training data is obtained it can undergo data transformation 207, data integration 209, and/or data reduction 211. Data transformation, integration and/or reduction can be used to identify and extract the features relevant to clinical outcomes and non-clinical parameters. For example, data transformation can include feature engineering techniques, data normalization or scaling, and encoding of categorical variables. Feature engineering can include the creation of new features or transformation of existing features to enhance model performance. Data normalization or scaling can include scaling numerical features to a standard range, such data from various sources can be combined. Encoding of categorical variables can include converting categorical data into numerical format using techniques like one-hot encoding or label encoding.

Data integration can include the process of merging or combining multiple datasets and ensuring consistency in keys or identifiers for merging. Data reduction can include applying techniques such as principal components analysis (PCA) to reduce higher-dimensional datasets. Data reduction can also include applying techniques such as features selection.

In some embodiments, the availability of training data is limited. For example, the available data from clinical trials may pose some limitations in terms of significant patient numbers for analysis. Accordingly, synthetic data can be generated to provide additional training data for the AI-models described herein. For example, synthetic data can be generated using generative AI with small data sets to generate larger data sets. Examples of generative AI models that can be used to generate synthetic training data include, but are not limited to, Generative Adversarial Networks (GANs) combined with Transfer Learning (TL) to generate synthetic data. For example, the GANs approach consists of two neural networks, the generator and the discriminator, working against each other. The generator creates synthetic data, and the discriminator distinguishes between real and synthetic data. The TL approach leverages pre-trained generative models made on larger datasets and fine-tuning them on smaller datasets. This approach uses the knowledge learned from larger datasets and adapts it to generate synthetic data in a specific domain. In this manner, synthetic training data can be generated using machine learning techniques and the generated synthetic training data can also be used to train further AI-models.

Figure 2B:
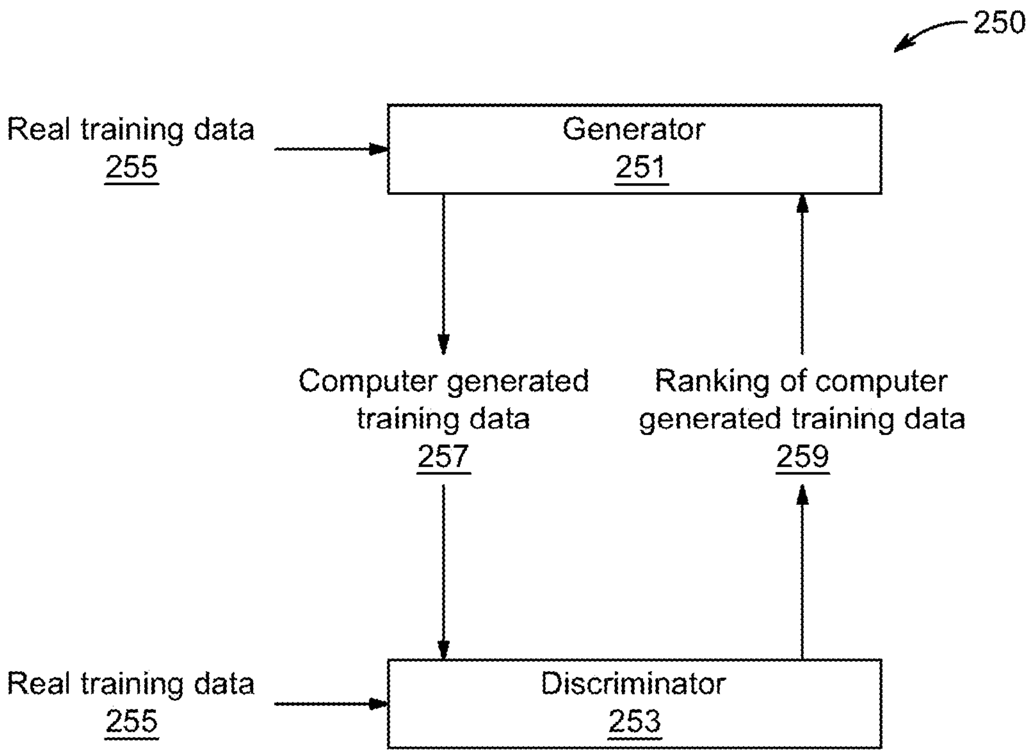
FIG. 2B is a block diagram illustrating generation of synthetic training data in accordance with some embodiments of the present disclosure.

FIG. 2B is a block diagram illustrating generation of synthetic training data 250. As depicted in FIG. 2B, in a training phase a generator neural network 251 is provided with real training data 255 and outputs computer generated training data 257. A discriminator neural network 253 evaluates the computer-generated training data 257 alongside the real training data 255 and provides the generator 251 with a ranking of the computer-generated training data 259 so that the generator 251 can improve its output. In this manner, iteratively, the generator can learn how to produce synthetic training data, which can be used with the machine learning approaches described herein.

In some embodiments, the training data described above can be used to train a machine learning software. For example, in some embodiments a machine learning software is trained using training data set and a target in a manner that might be described as supervised learning. In these embodiments, the data set is conventionally divided into a training set, a test set, and, in some cases, a validation set. A target is specified that contains the correct classification of each input value in the data set. for each sample presented during training, the output generated by the machine learning software module is compared with the desired target. The difference between the target and the set of input samples is calculated, and the machine learning software module is modified to cause the output to more closely approximate the desired target value. In some embodiments, a back-propagation algorithm is utilized to cause the output to more closely approximate the desired target value. After a large number of training iterations, the machine learning software module output will closely match the desired target for each sample in the input training set. Subsequently, when new input data, not used during training, is presented to the machine learning software module, it may generate an output classification value indicating which of the categories the new sample is most likely to fall into. The machine learning software module is said to be able to "generalize" from its training to new, previously unseen input samples. This feature of a machine learning software module allows it to be used to classify almost any input data which has a mathematically relationship to the category to which it should be assigned.

Alternatively, in some embodiments, the machine learning software can be trained using unsupervised learning techniques, where the machine learning software or algorithm can be provided with data and allowed to discover patterns and insights without guidance or instruction. Machine learning software modules that are commonly used for unsupervised training include k-means clustering, mixtures of multinomial distributions, affinity propagation, discrete factor analysis, hidden Markov models, Boltzmann machines, restricted Boltzmann machines, autoencoders, convolutional autoencoders, recurrent neural network autoencoders, and long short-term memory autoencoders. While there are many unsupervised learning models, they all have in common that, for training, they require a training set without associated labels or targets.

In some embodiments, an artificial intelligence (AI) based model is trained to output a ranking of the most influential process parameters in affecting patient response based on the received training data. AI based models can include machine learning models, deep learning models, and the like. In some embodiments, the artificial intelligence (AI) based models trained herein are capable of producing outputs indicating a predicted response for a set of process parameters and/or a ranking of the process parameters determined to be most impactful in generating improved cell products. Outputs of the trained artificial intelligence models can include model performance indicators like the confusion matrix, the receiver operating curve (ROC), the area under the ROC (AUC), precision, F1, positive predictive values (PPV), negative predictive value (NPV), precision, accuracy, sensitivity, and specificity, among others. Outputs to confirm the model performance can indicate the most impactful features based on relative feature weights accompanied by SHAP (SHapley Additive explanations) values to show how each feature affects each final prediction, the significance of each feature compared to others, and model reliance on the interaction between features. Alternatively, or additionally, outputs can include local interpretable model-agnostic explanations (LIME) which can approximate any black box machine learning model with a local, interpretable model to explain each individual prediction to be visualized in a more readily explainable manner.

Figure 3:
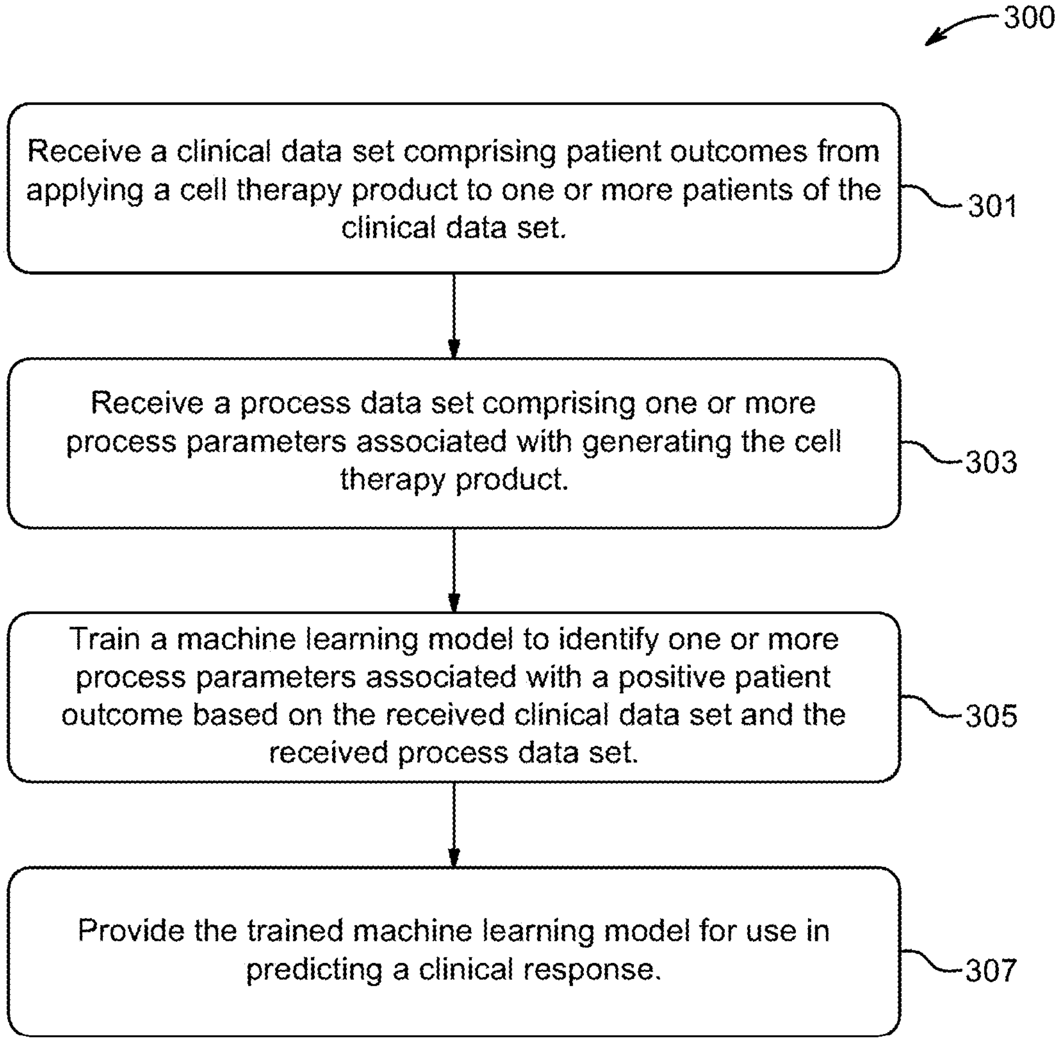
FIG. 3 is a flow-chart for training a machine learning model in accordance with some embodiments of the present disclosure.

FIG. 3A illustrates a method for training an artificial intelligence/machine-learning based model. As shown in FIG. 3A, a method 300 can include the steps of receiving a clinical data set comprising patient outcomes from applying a cell therapy product to one or more patients of the clinical data set 301, receiving a process data set comprising one or more process parameters associated with generating the cell therapy product 303, training a machine learning model to identify one or more process parameters associated with a positive patient outcome based on the received clinical data set and the received process data set 305, and providing the trained machine learning model for use in predicting a clinical response 307.

Clinical data set and the process data set can include the training data discussed above. In some embodiments, the clinical data set includes at least one of: patient outcomes data, or patient demographic data.

Patient outcomes data can include a data set including one or more parameters indicating complete response (CR), partial response (PR), stable disease (SD), progressive disease (PD), overall response rate (ORR), duration of response (DoR), time to progression (TTP), time to treatment failure (TTF), and/or survival rates. Patient outcomes data can include data represented as Booleans, numerical values, percentages, or the like. Complete response may correspond to the complete disappearance of all detectable cancer in response to treatment. Partial response (PR) can indicate a significant reduction in the size of measurable tumors, typically by a predefined percentage (e.g., 30% or more), in response to treatment. Stable disease (SD) can indicate that the cancer neither shrinks nor grows significantly during treatment. Progressive disease (PD) can indicate that the cancer grows or spreads despite treatment, indicating that the cell therapy treatment is not effectively controlling the disease. Overall response rate (ORR) can indicate the proportion of patients who achieve a complete or partial response to treatment. Duration of response (DoR) can indicate the length of time from the initial response to treatment until disease progression or recurrence. Time to progression (TTP) can indicate the time from the start of treatment until the cancer begins to progress or worsen. Time to treatment failure (TTF) can indicate the time from the start of treatment until the patient stops treatment due to disease progression, intolerable side effects, or other reasons. Survival rates may provide a measure of how long patients live after diagnosis or treatment.

Patient demographic data can include gender, age, address, insurance, health data, weight, height, race, ethnicity, and the like.

In some embodiments, as discussed above, the training data includes in vitro assay results of the cell engineering process, where the in vitro assay results include one or more of a cell number, percentage phenotype, cell recovery data, cell diameter, hold time, expansion properties of the engineered cells, persistence properties of the engineered cells, cytokine release patterns, or cytotoxicity levels in vitro. Additionally, the training data can include process data including at least one of: operator identification, initial volume, donor, mixing, dilution speed, input bag rinsing, optical cell detection, product filing speed, waste extraction speed, intermediate volume, pre-wash cycles, pre-wash g-force, pre-wash sedimentation time, or switch washing solution.

Training AI-based models can involve the use of benchmark datasets containing known critical process parameters. For example, AI-based models can be provided with labeled data to learn patterns and relationships between process parameters and clinical responses and/or cell properties. The cell therapy product can be a chimeric antigen receptor (CAR) T cell.

In some embodiments, a plurality of artificial intelligence models are trained using different training data sets. Examples of artificial intelligence models include, but are not limited to XGboost, LightGBM, Random Forests, RulesFit, Linear Learner, ElasticNet, KerasSlim NN, and k-NNs. The artificial intelligence model can include logistic regression, an elastic net, a k-nearest neighbor, a decision tree, a random forest, a support vector machine, a support vector, a light gradient boosting method, an extreme gradient boosting method, or a multi-layer perceptron.

Figure 4A:
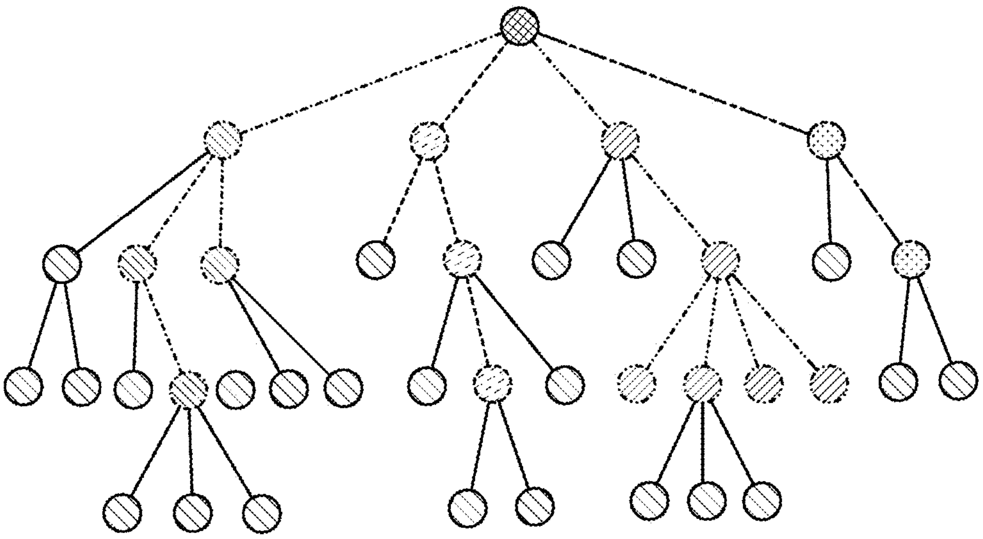
FIG. 4A is a schematic illustration of a first artificial intelligence model (e.g., decision tree) in accordance with some embodiments of the present disclosure.

FIGS. 4A-4D provide illustrations of the computer architecture of artificial intelligence models trained herein. For example, FIG. 4A illustrates a decision tree model. As shown, predictions can be generated by recursively splitting the data into subsets based on the most significant feature at each node of the tree.

Figure 4B:
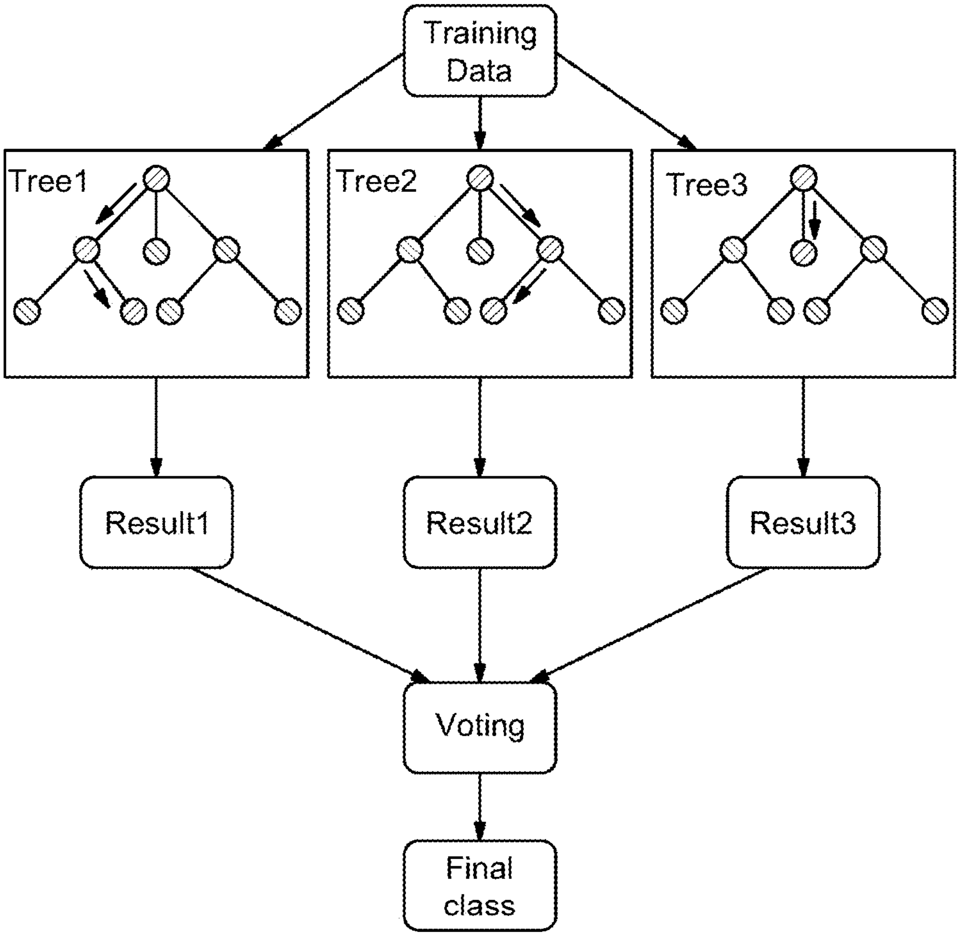
FIG. 4B is a schematic illustration of a second artificial intelligence model (e.g., forest) in accordance with some embodiments of the present disclosure.

In some embodiments, a random forest model is used. As shown in FIG. 4B, a random forest can include a plurality of decision trees. For example, multiple bootstrap samples (random samples with replacement) can be created from the original dataset. Each bootstrap sample is used to train a separate decision tree. For each decision tree in the ensemble, a random subset of features is selected at each node for determining the best split. This introduces diversity among the trees and helps prevent overfitting. Each decision tree is trained independently on one of the bootstrap samples using the random subset of features. The tree is grown by recursively partitioning the data based on feature values until a stopping criterion is met. During the prediction phase, each tree in the ensemble predicts the outcome for a given input. For classification tasks, the class with most votes across all trees is considered the final prediction. For regression tasks, the average prediction from all trees is taken. Accordingly, a random forest model can be used as an artificial intelligence based model for producing classification or regression based outcomes.

Figure 4C:
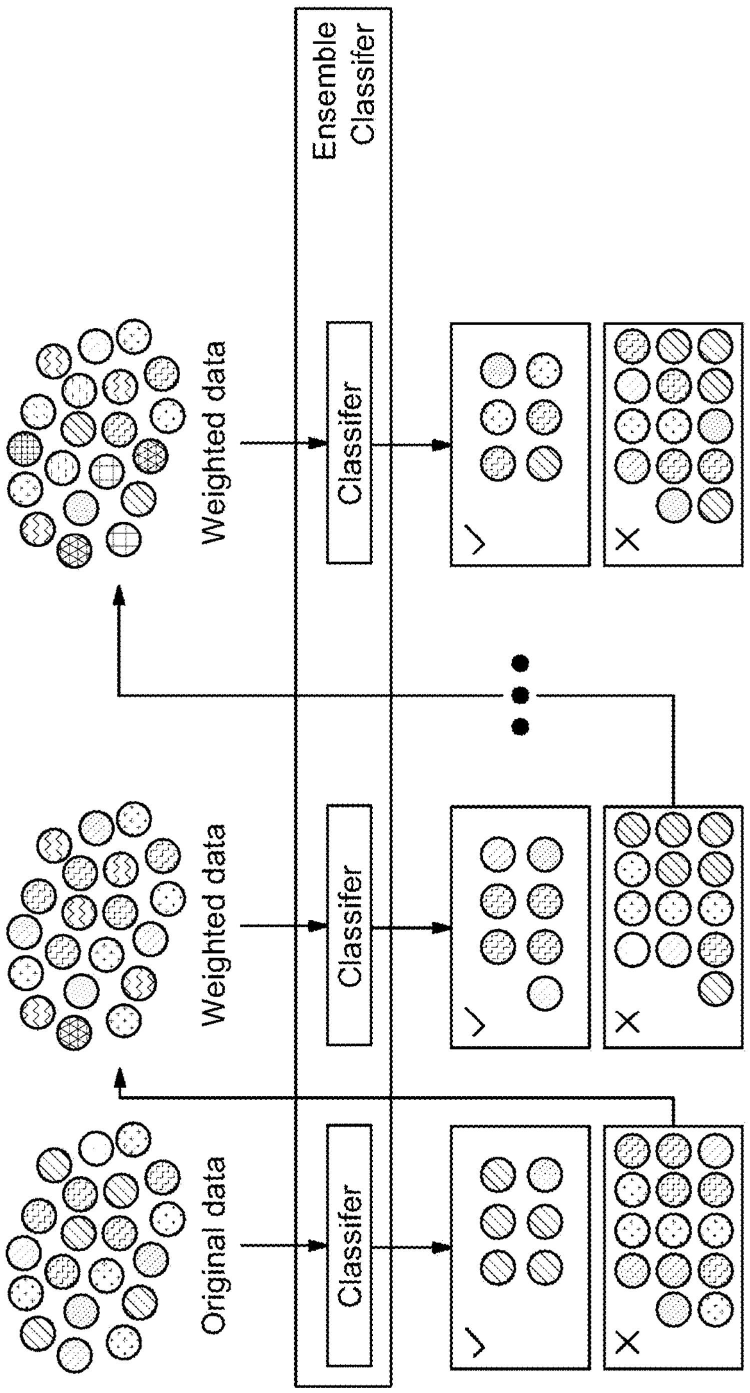
FIG. 4C is a schematic illustration of a third artificial intelligence model (e.g., XGBoost) in accordance with some embodiments of the present disclosure.

In some embodiments, an XGBoost (or eXtreme Gradient Boosting) algorithm is applied to process development data. FIG. 4C provides a schematic illustration of the architecture for XGBoost. For example, an XGBoost algorithm can repeatedly build a collection of decision trees. The XGBoost model can manage missing data by capturing non-linear correlations between model features and outcomes and accommodate higher-order interactions among variables. XGBoost can utilize multiple weak learners (usually decision trees) and combine them to create a stronger predictive model. It may build trees sequentially, where each subsequent tree corrects the errors made by the previous one. XGBoost primarily uses decision trees as base learners, which are simple models that make sequential splits based on features to predict the target variable. The XGBoost algorithm can be configured to handle less than perfect data, with missing values within datasets, allowing it to learn from missing data during training. It includes L1 (lasso regression) and L2 (ridge regression) regularization terms in the objective function to control overfitting. This helps in building models that generalize well to new, unseen data. XGBoost can be highly efficient due to its ability to leverage parallel computing, making it faster compared to traditional gradient boosting implementations. XGBoost can also use a technique called tree pruning, where the algorithm prunes trees during the building process if they do not contribute significantly to improving the model's performance, thus preventing overfitting. XGBoost can provide improved performance over other methods. For example, XGBoost often outperforms other algorithms due to its ability to handle large datasets efficiently and its robustness to overfitting. XGBoost also provides a feature importance score, allowing users to understand which features are most relevant in making predictions.

In some embodiments, the AI-based model includes a LightGBM model which is capable of operating at efficient speeds, with low memory usage. The LightGBM model can provide improved performance for categorial features. However, it may be limited by small datasets, be sensitive to hyperparameters and may be prone to some degree of overfitting.

In some embodiments, the AI-based model includes a RulesFit model that generates human-interpretable rules that are easily explainable, and feature importance can be extracted and provide less overfitting. However, the simplicity of the RulesFit model may limit accuracy, require high quality data, and continuous variables may pose challenges to the model.

In some embodiments, the AI-based model includes ElasticNets that are configured to handle high-dimensional data, sparsity, and multiple correlated predictors well. However, this model can be difficult to interpret, and require complex hyperparameters and computational power.

In some embodiments, the AI-based model includes a KerasSlimNN model which is efficient, easily deployed and allows for faster training. However, this model may have reduced flexibility and accuracy.

In some embodiments, the AI-based model includes a deep learning model such as a multi-layer perceptron.

In some embodiments, the AI-based model includes a k-nearest neighbor model which is simple and does not require extensive "training" and is also flexible with its data requirements. However, the k-nearest neighbor model can be sensitive to noise, outliers, require scaling and normalization, and may not do well with larger data sets.

Figure 4D:
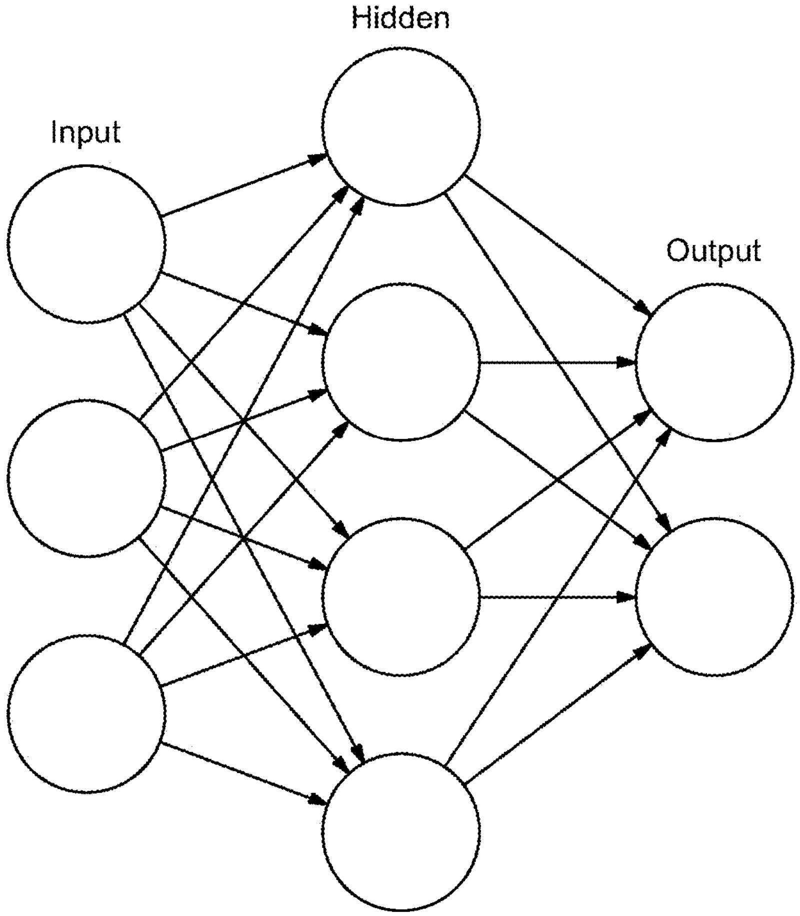
FIG. 4D is a schematic illustration of a fourth artificial intelligence model (e.g., neural network) in accordance with some embodiments of the present disclosure.

FIG. 4D illustrates a neural network AI-model, with a hidden layer in between an input layer and an output layer.

Figure 4E:
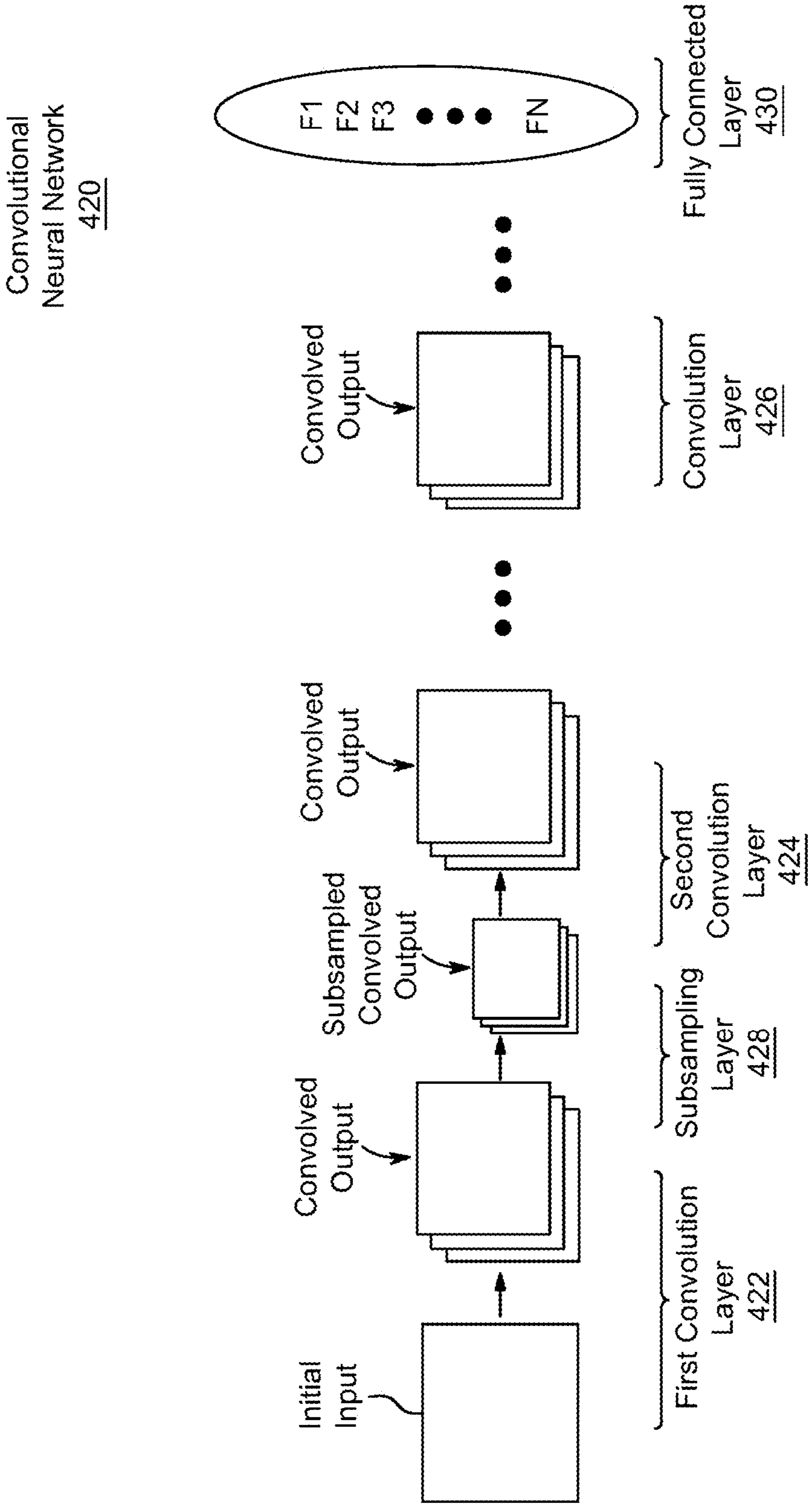
FIG. 4E is a schematic illustration of a fifth artificial intelligence model (e.g., a convolutional neural network) in accordance with some embodiments of the present disclosure.

FIG. 4E shows an implementation of a machine learning model. More specifically, illustrated is a diagram of an implementation of a convolutional neural network (CNN) 420. While CNN 420 includes certain features as described herein, these features are provided for the purpose of illustration and are not intended to limit the present disclosure.

CNN 420 includes a plurality of convolution layers including first convolution layer 422, second convolution layer 424, and convolution layer 426. In some embodiments, CNN 420 includes sub-sampling layer 428 (sometimes referred to as a pooling layer). In some embodiments, sub-sampling layer 428 and/or other subsampling layers have a dimension (e.g., an amount of nodes) that is less than a dimension of an upstream system. By virtue of sub-sampling layer 428 having a dimension that is less than a dimension of an upstream layer, CNN 420 consolidates the amount of data associated with the initial input and/or the output of an upstream layer to thereby decrease the amount of computations necessary for CNN 420 to perform downstream convolution operations. Additionally, or alternatively, by virtue of sub-sampling layer 428 being associated with (e.g., configured to perform) at least one subsampling function (as described below with respect to FIGS. 4F and 4G), CNN 420 consolidates the amount of data associated with the initial input.

Convolution operations are performed based on respective inputs and/or outputs associated with each of first convolution layer 422, second convolution layer 424, and convolution layer 426 to generate respective outputs. In some examples, data is provided as input to first convolution layer 422, second convolution layer 424, and convolution layer 426. A detailed description of convolution operations is included below with respect to FIG. 4F.

In some embodiments, data associated with an input (referred to as an initial input) is provided to first convolution layer 422 data associated with an output is generated using first convolution layer 422. In some embodiments, an output generated by a convolution layer is provided as input to a different convolution layer. For example, the output of first convolution layer 422 is provided as input to sub-sampling layer 428, second convolution layer 424, and/or convolution layer 426. In such an example, first convolution layer 422 is referred to as an upstream layer and sub-sampling layer 428, second convolution layer 424, and/or convolution layer 426 are referred to as downstream layers. Similarly, in some embodiments the output of sub-sampling layer 428 is provided to second convolution layer 424 and/or convolution layer 426 and, in this example, sub-sampling layer 428 would be referred to as an upstream layer and second convolution layer 424 and/or convolution layer 426 would be referred to as downstream layers.

In some embodiments, CNN 420 generates an output based on convolution operations associated with each convolution layer. In some examples, CNN 420 generates an output based on convolution operations associated with each convolution layer and an initial input. In some embodiments, the output of convolution layer 426 is provided as fully connected layer 430. In some examples, the output of convolution layer 426 is provided as fully connected layer 430, where fully connected layer 430 includes data associated with a plurality of feature values referred to as F1, F2 . . . . FN. In this example, the output of convolution layer 426 includes data associated with a plurality of output feature values that represent a prediction.

In some embodiments, a prediction is identified from among a plurality of predictions based on identification of a feature value that is associated with the highest likelihood of being the correct prediction from among the plurality of predictions. For example, where fully connected layer 430 includes feature values F1, F2, . . . . FN, and F1 is the greatest feature value, the prediction associated with F1 is identified as being the correct prediction from among the plurality of predictions. In some embodiments, CNN 420 is trained to generate the prediction. In some examples, CNN 420 is trained to generate the prediction based on training data associated with the prediction being provided to CNN 420.

Figure 4F:
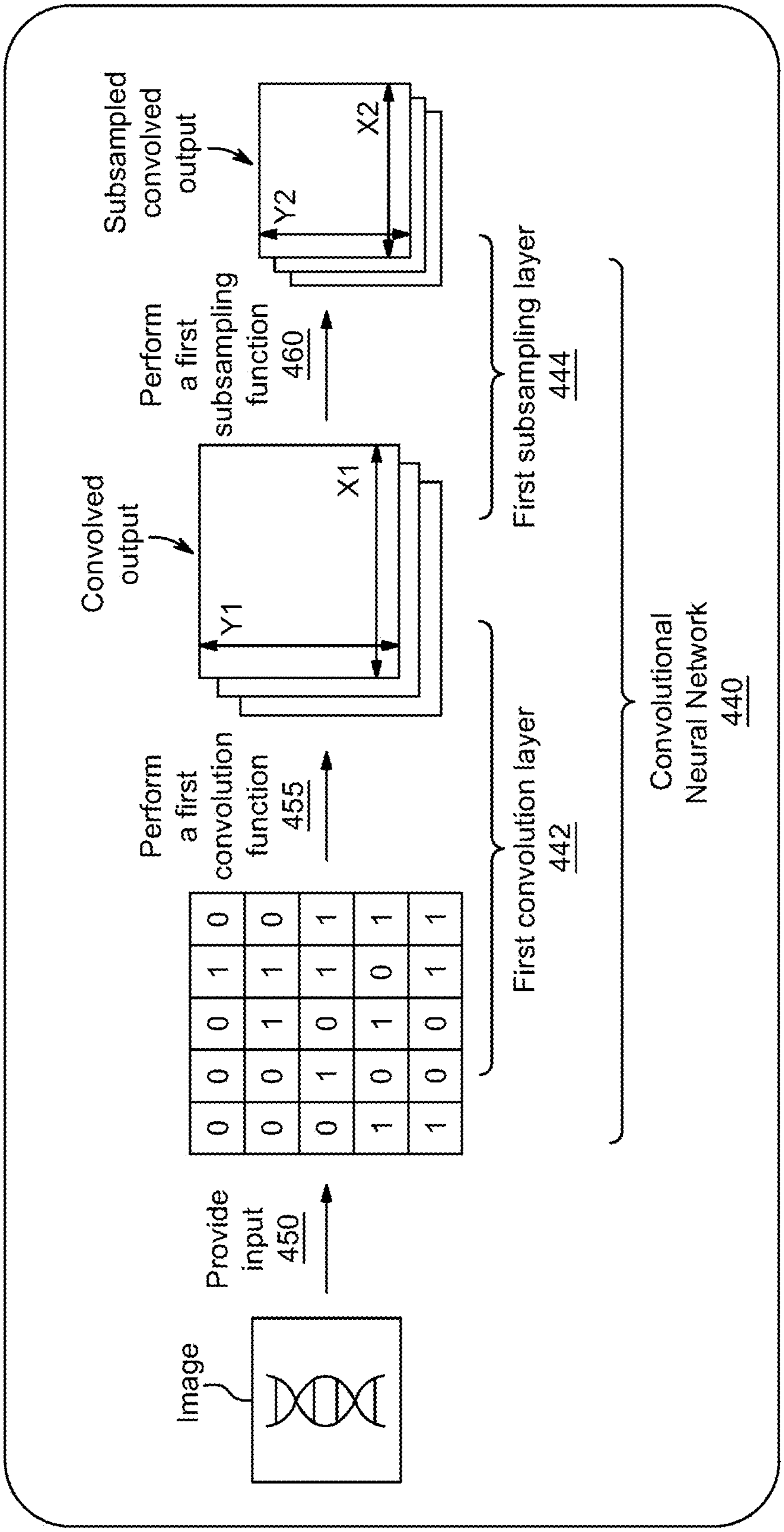
FIG. 4F is a second schematic illustration of a fifth artificial intelligence model (e.g., a convolutional neural network) in accordance with some embodiments of the present disclosure.
Figure 4G:
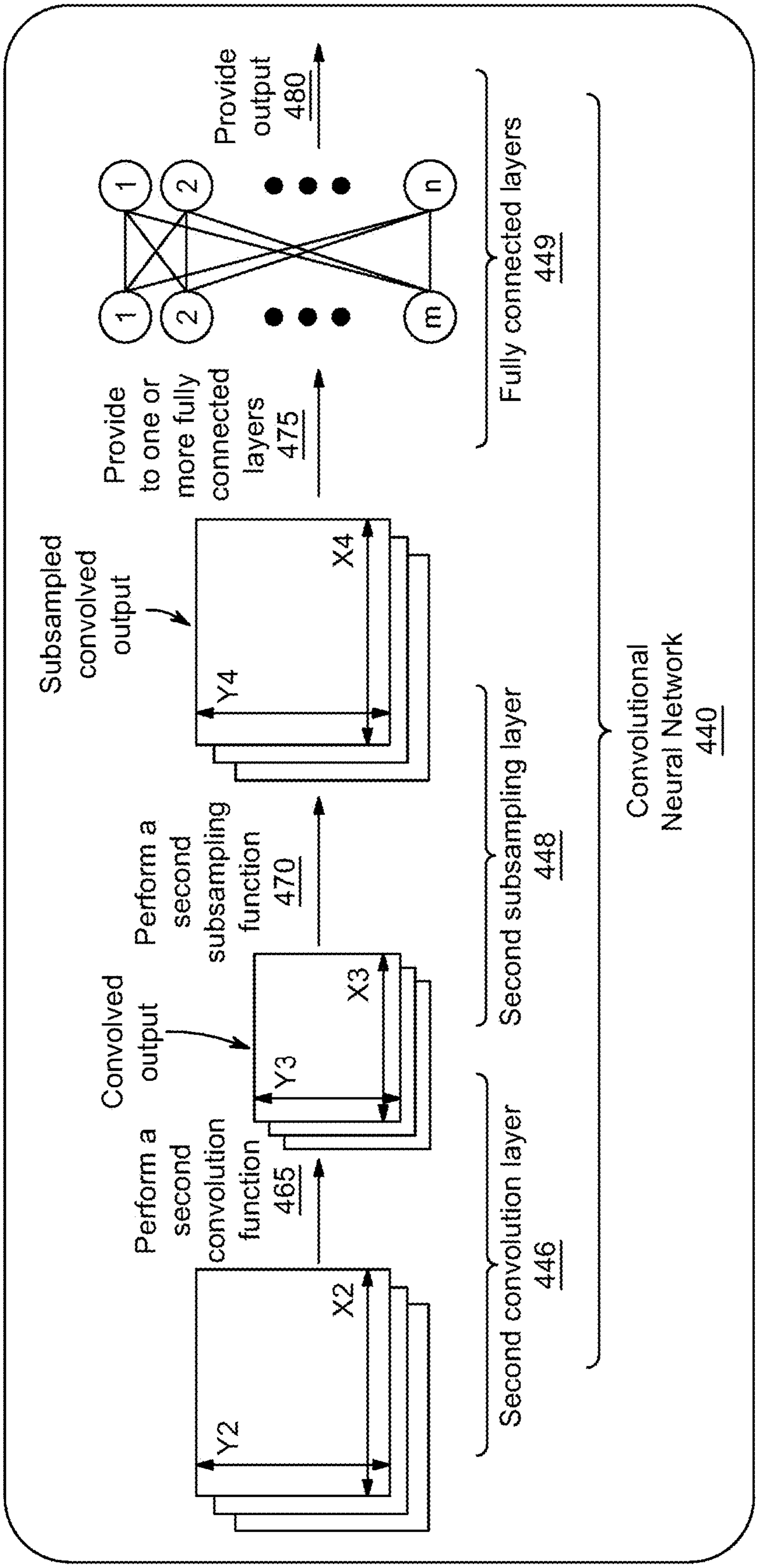
FIG. 4G is a third schematic illustration of a fifth artificial intelligence model (e.g., a convolutional neural network) in accordance with some embodiments of the present disclosure.

Referring now to FIGS. 4F and 4G, illustrated is a diagram of example operation of CNN 440. In some embodiments, CNN 440 (e.g., one or more components of CNN 440) is the same as, or similar to, CNN 420 (e.g., one or more components of CNN 420) (see FIG. 4E).

At step 450, data associated with an image is provided as input to CNN 440 (step 450). For example, as illustrated, the data associated with the image is provided to CNN 440, where the image is a greyscale image represented as values stored in a two-dimensional (2D) array. In some embodiments, the data associated with the image may include data associated with a color image, the color image represented as values stored in a three-dimensional (3D) array. Additionally, or alternatively, the data associated with the image may include data associated with an infrared image, a radar image, and/or the like.

At step 455, CNN 440 performs a first convolution function. For example, CNN 440 performs the first convolution function based on CNN 440 providing the values representing the image as input to one or more neurons (not explicitly illustrated) included in first convolution layer 442. In this example, the values representing the image can correspond to values representing a region of the image (sometimes referred to as a receptive field). In some embodiments, each neuron is associated with a filter (not explicitly illustrated). A filter (sometimes referred to as a kernel) is representable as an array of values that corresponds in size to the values provided as input to the neuron. In one example, a filter may be configured to identify edges (e.g., horizontal lines, vertical lines, straight lines, and/or the like). In successive convolution layers, the filters associated with neurons may be configured to identify successively more complex patterns (e.g., arcs, objects, and/or the like).

In some embodiments, CNN 440 performs the first convolution function based on CNN 440 multiplying the values provided as input to each of the one or more neurons included in first convolution layer 442 with the values of the filter that corresponds to each of the one or more neurons. For example, CNN 440 can multiply the values provided as input to each of the one or more neurons included in first convolution layer 442 with the values of the filter that corresponds to each of the one or more neurons to generate a single value or an array of values as an output. In some embodiments, the collective output of the neurons of first convolution layer 442 is referred to as a convolved output. In some embodiments, where each neuron has the same filter, the convolved output is referred to as a feature map.

In some embodiments, CNN 440 provides the outputs of each neuron of first convolutional layer 442 to neurons of a downstream layer. For purposes of clarity, an upstream layer can be a layer that transmits data to a different layer (referred to as a downstream layer). For example, CNN 440 can provide the outputs of each neuron of first convolutional layer 442 to corresponding neurons of a subsampling layer. In an example, CNN 440 provides the outputs of each neuron of first convolutional layer 442 to corresponding neurons of first subsampling layer 444. In some embodiments, CNN 440 adds a bias value to the aggregates of all the values provided to each neuron of the downstream layer. For example, CNN 440 adds a bias value to the aggregates of all the values provided to each neuron of first subsampling layer 444. In such an example, CNN 440 determines a final value to provide to each neuron of first subsampling layer 444 based on the aggregates of all the values provided to each neuron and an activation function associated with each neuron of first subsampling layer 444.

At step 460, CNN 440 performs a first subsampling function. For example, CNN 440 can perform a first subsampling function based on CNN 440 providing the values output by first convolution layer 442 to corresponding neurons of first subsampling layer 444. In some embodiments, CNN 440 performs the first subsampling function based on an aggregation function. In an example, CNN 440 performs the first subsampling function based on CNN 440 determining the maximum input among the values provided to a given neuron (referred to as a max pooling function). In another example, CNN 440 performs the first subsampling function based on CNN 440 determining the average input among the values provided to a given neuron (referred to as an average pooling function). In some embodiments, CNN 440 generates an output based on CNN 440 providing the values to each neuron of first subsampling layer 444, the output sometimes referred to as a subsampled convolved output.

At step 465, CNN 440 performs a second convolution function. In some embodiments, CNN 440 performs the second convolution function in a manner similar to how CNN 440 performed the first convolution function, described above. In some embodiments, CNN 440 performs the second convolution function based on CNN 440 providing the values output by first subsampling layer 444 as input to one or more neurons (not explicitly illustrated) included in second convolution layer 446. In some embodiments, each neuron of second convolution layer 446 is associated with a filter, as described above. The filter(s) associated with second convolution layer 446 may be configured to identify more complex patterns than the filter associated with first convolution layer 442, as described above.

In some embodiments, CNN 440 performs the second convolution function based on CNN 440 multiplying the values provided as input to each of the one or more neurons included in second convolution layer 446 with the values of the filter that corresponds to each of the one or more neurons. For example, CNN 440 can multiply the values provided as input to each of the one or more neurons included in second convolution layer 446 with the values of the filter that corresponds to each of the one or more neurons to generate a single value or an array of values as an output.

In some embodiments, CNN 440 provides the outputs of each neuron of second convolutional layer 446 to neurons of a downstream layer. For example, CNN 440 can provide the outputs of each neuron of first convolutional layer 442 to corresponding neurons of a subsampling layer. In an example, CNN 440 provides the outputs of each neuron of first convolutional layer 442 to corresponding neurons of second subsampling layer 448. In some embodiments, CNN 440 adds a bias value to the aggregates of all the values provided to each neuron of the downstream layer. For example, CNN 440 adds a bias value to the aggregates of all the values provided to each neuron of second subsampling layer 448. In such an example, CNN 440 determines a final value to provide to each neuron of second subsampling layer 448 based on the aggregates of all the values provided to each neuron and an activation function associated with each neuron of second subsampling layer 448.

At step 470, CNN 440 performs a second subsampling function. For example, CNN 440 can perform a second subsampling function based on CNN 440 providing the values output by second convolution layer 446 to corresponding neurons of second subsampling layer 448. In some embodiments, CNN 440 performs the second subsampling function based on CNN 440 using an aggregation function. In an example, CNN 440 performs the first subsampling function based on CNN 440 determining the maximum input or an average input among the values provided to a given neuron, as described above. In some embodiments, CNN 440 generates an output based on CNN 440 providing the values to each neuron of second subsampling layer 448.

At step 475, CNN 440 provides the output of each neuron of second subsampling layer 448 to fully connected layers 449. For example, CNN 440 provides the output of each neuron of second subsampling layer 448 to fully connected layers 449 to cause fully connected layers 449 to generate an output. In some embodiments, fully connected layers 449 are configured to generate an output associated with a prediction (sometimes referred to as a classification). The prediction may include an indication that an object included in the image provided as input to CNN 440 includes an object, a set of objects, and/or the like.

In some embodiments, the AI-based models are used to generate output based on specific data features expressed as multiclass or binary classifiers. These models will be further trained using the integrated dataset, and the best-performing models are chosen through k-fold cross-validation or a log-loss based analysis. To assess their performance, indicators like the AUC of the receiver operating curve (ROC), sensitivity/specificity, impactful features, positive/negative predictive values, the F1 statistic, accuracy, and other relevant metrics can be evaluated. The AI-based models can be configured to generate the AUC of the ROC, sensitivity/specificity, ranking of impactful features, positive/negative predictive values, F1 statistics and the like.

AI-based models can be evaluated for their performance. For example, best performing models can be chosen through k-fold cross-validation, or log-loss analysis. Performance of the AI-based models can be evaluated based on indicators like the AUC of the receiver operating curve (ROC), sensitivity/specificity, impactful features, positive/negative predictive values, the F1 statistic, accuracy, and other relevant metrics, which are all central outputs from an AI/ML based approach.

In some embodiments, the trained AI-models are validated to prevent over-fitting to the training data. In some embodiments k-fold cross-validation of the trained model are used to prevent over-fitting. In one example, the described machine learning models are trained on eighty percent of a data set and validated on twenty percent of the data set (used as a holdout). The best performing machine learning models and/or their respective parameters, can be selected based on the results of a cross-validation or log-loss based analysis. For example, a ten-fold cross-validation method can be used. Different random seeds can be used to confirm the validity of the data. For example, in some embodiments, training the AI model involves partitioning the training dataset into k equally sized subsets (or "folds")

and iteratively using these subsets for training and validation. In addition, the dataset is separated into three parts: training, validation, and test subsets. This allows for training on the training subset, tuning hyperparameters for the AI models on the validation subset, and evaluating the model's performance on the test subset, which the model has not accessed prior to testing.

In some embodiments, a specialized cross-validation process is performed. In some embodiments, the training data includes both real and synthetic data generated in accordance with the methods and systems described above. A specialized cross-validation process can be used to minimize the bias associated with the random division of data into training and testing sets when the data set is small in size. The specialized cross-validation process can include the steps of hyperparameter tuning, model evaluation, performance assessment, and the like. For example, hyperparameter tuning can include an inner loop with 3-folds or subsections and can be used to determine settings for the model by evaluating its performance. Model evaluation can utilize an outer loop that divides data into 5-separate folds or subsections. A two-layered loop system for hyperparameter tuning and model evaluation that includes 3 folds inside for fine-tuning the model, and 5 folds outside for evaluation, can provide a thorough and reliable validation method.

The cross-validation process can evaluate an artificial intelligence model's performance through the entire nested cross-validation process. For example, the average accuracy and the area under the Receiver Operating Characteristic (ROC) curve can be analyzed across all the outer folds. Thus, the algorithm's overall performance through this detailed cross-validation procedure is analyzed. Further, fine-tuning the model's hyperparameters can be done within the inner loop. After performance is assessed, the best set of hyperparameters is chosen by using a separate 10-fold cross-validation on the whole dataset. The division of training and testing data is managed by k-fold cross-validation. The models are trained on k−1 of the folds and validated on the remaining fold, which eliminates the need for a separate training and testing split.

The machine learning models can be validated prior to the trained machine learning model being applied on process parameter data.

Data for process parameters can be received at the trained AI model. The trained AI model can then produce output including an identification of the process parameters likely to impact response, in accordance with an application phase of the machine learning model. For example, a trained machine learning model, such as that trained by the process in FIG. 3, can be applied to a set of process parameters to identify at least a set of process parameters that can be improved.

Data for process parameters can also be received at the trained AI model, such that by applying the trained AI model to the received data, the AI model outputs a prediction of the response elicited by the cells generated in accordance with the received process parameters.

In some embodiments, the data including the process parameters received at the AI model can be pre-processed including cleaning, transformation, integration, and reduction in accordance with the methods described above with respect to pre-processing the training data.

In some embodiments, the disclosed systems and methods can be used to optimize and/or improve the development of cell therapy processes, and in turn improve patient responses to treatment. For example, output from the one or more machine learning models can be used to generate a treatment plan for a patient. Further, output from the one or more machine learning models can be used to alter a process parameter, or a setting for a machine involved in the process for engineering cells. By applying a machine learning model and providing visual representations of the machine learning models to data, an intuitive interface for understanding complex information is provided that can aid in quick decision-making and facilitates the identification of bottlenecks or areas for improvement in the cell therapy development pipeline.

Output from applying the trained artificial intelligence models, including machine learning and deep learning models, can be used to forecast optimal cell culture conditions, media formulations, and scaling strategies in the cell engineering process. Accordingly, the process for engineering cells such as CAR-T cells can be improved with enhanced efficiency, reduced expenses, and enhanced quality.

Figure 5:
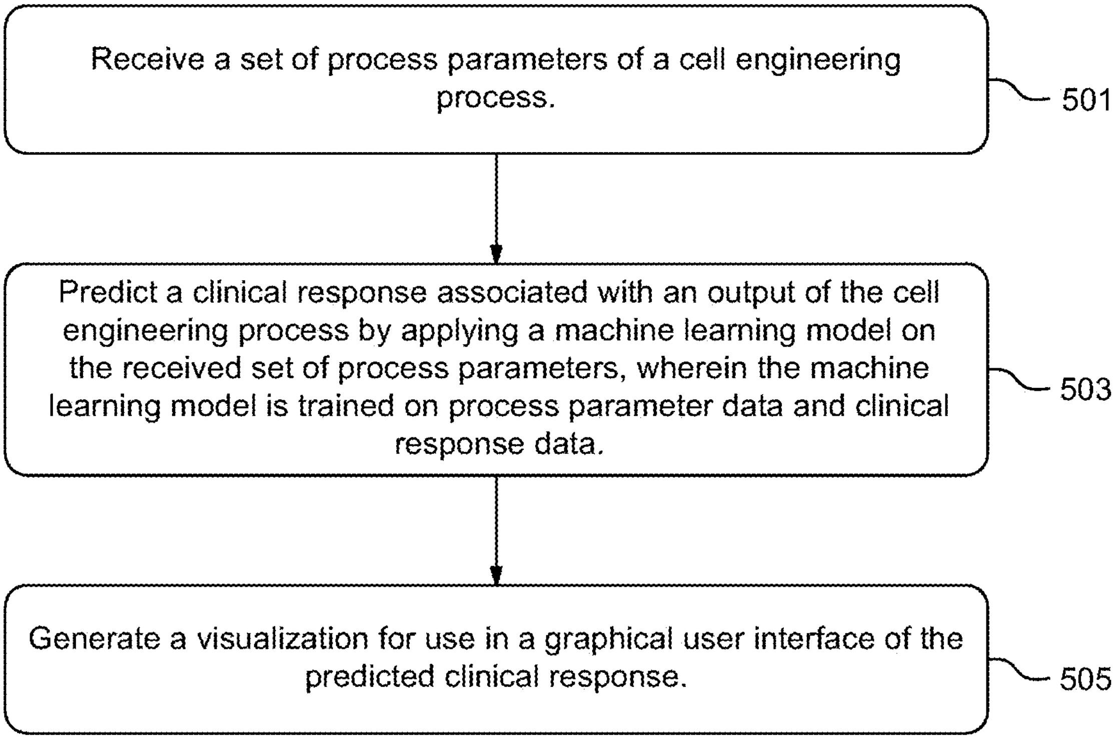
FIG. 5 is a flow-chart for applying a machine learning model in accordance with some embodiments of the present disclosure.

FIG. 5 illustrates a process for applying a trained machine learning model. As illustrated in FIG. 5, a process 500 includes the steps of receiving a set of process parameters of a cell engineering process 501, predicting a clinical response associated with an output of the cell engineering process by applying a machine learning model to the received set of process parameters 503, where the machine learning model is trained on process parameter data and clinical response data, and generating a visualization for use in a graphical user interface of the predicted clinical response 505.

As discussed with respect to training data, in some embodiments the set of process parameters includes at least one of: operator identification, initial volume, donor, mixing, dilution speed, input bag rinsing, optical cell detection, product filing speed, waste extraction speed, intermediate volume, pre-wash cycles, pre-wash g-force, pre-wash sedimentation time, switch washing solution, lactate concentration, oxygen concentration, $CO_2$ concentration, hold time prior to freeze, cell freezing parameters, and thaw parameters.

Further, the trained machine learning model can include at least one of logistic regression, an elastic net, a k-nearest neighbor, a decision tree, a random forest, a support vector machine, a support vector, a light gradient boosting method, an extreme gradient boosting method, or a multi-layer perceptron. The trained machine learning model can be trained on clinical response data including at least one of patient outcomes data, or patient demographic data. The trained machine learning model was trained on in vitro assay results of the cell engineering process, wherein the in vitro assay results comprise one or more of a cell number, percentage phenotype, cell recovery data, cell diameter, hold time, expansion properties of the engineered cells, persistence properties of the engineered cells, cytokine release patterns, or cytotoxicity levels in vitro.

In some embodiments, one or more parameters of the cell engineering process are adjusted based on the predicted clinical response. Further, a set of cells can be generated based on a cell engineering process having the adjusted parameters.

In some embodiments, the visualization tool provides developers and process engineers the ability to visualize and better understand the most critical process parameters for a given cell therapy. In some embodiments, the visualization includes a simulation tool that allows for the simulation of how different changes in the process can impact patient treatment outcomes. The visualization and/or simulation tool can be configured for use by non-data scientists. Users of the visualization tools can include clinicians, process development scientists, and the like.

The visualization tool can include a graphical user interface. The graphical user interface can be configured to display the predicted clinical response and at least one of: one or more characteristics of the trained machine learning model, or the received set of process parameters.

In some embodiments, the visualization tool may include a large language foundational model that allows a user to interact with the machine learning models, and data. The large language foundational model can enhance the user experience by providing an interactive interface that interprets and presents complex data insights in a conversational manner. This may aid in the understanding and development of critical parameter for process parameters. The large language foundational model can be used for explainability, text extraction, and for generating simulations.

For example, the visualization tool described herein allows for the visualization of the most impactful process parameters using a plurality of machine learning algorithms in a user-friendly interface. In addition, the interface will provide the option to perform simulations to further understand how changes to process parameters can potentially impact patient responses.

The visual representations of analyzed data can provide an intuitive interface for understanding complex information and aid in quick decision-making and facilitates the identification of bottlenecks or areas for improvement in the cell therapy development pipeline. For example, a web-based AI/ML visualization data tool for CAR-T process development and clinical data can allow scientists in the field to better understand process and clinical response and allow in silico manipulation for process run simulations.

The user interface can be improved to make the machine learning and artificial intelligence models used herein more accessible and explainable. For example, explainability metrics such as SHAP values can be provided to a user. SHAP values provide a method for obtaining a clear and unbiased understanding of how each feature influences a model prediction or output. SHAP values assign significance to each feature within a model. Features with positive SHAP values contribute positively to the prediction, whereas those with negative values exert a negative influence. The magnitude of these values indicates the strength of the effect. Importantly, SHAP values are model agnostic, making them applicable for interpreting any machine learning model.

In some embodiments, the systems and methods described herein are integrated into existing workflows and systems in cell therapy facilities.

In some embodiments, the systems and methods described herein are used to generate personalized treatment plans. For example, by evaluating patient clinical features in the context of the hundreds of measured features associated with the process may permit insights into parameters that can be manipulated during cell therapy development to maximize treatment success for individual patients. A personalized approach that integrates significant amounts of data derived from the entire process with multiple findings across different studies or cohorts can strengthen the understanding and potential predictive power of in vitro efficacy in predicting clinical responses to CAR-T therapy.

In some embodiments, user feedback can be used to modify and/or update the trained AI-model. For example, the graphical interface allows users to modify and update the underlying AI models that were trained. In some embodiments this can include hyperparameter tuning, which contributes towards optimizing model performance by finding the best set of hyperparameters. In other embodiments, techniques including grid search, random search, Bayesian optimization, and advanced optimization methods, can be employed to efficiently search the hyperparameter space and identify optimal configurations. In some embodiments, the visualization tool described herein can integrate automated approaches to hyperparameter tuning to further streamline the model development process and democratize machine learning for broader adoption by non-data scientists.

Figure 6A:
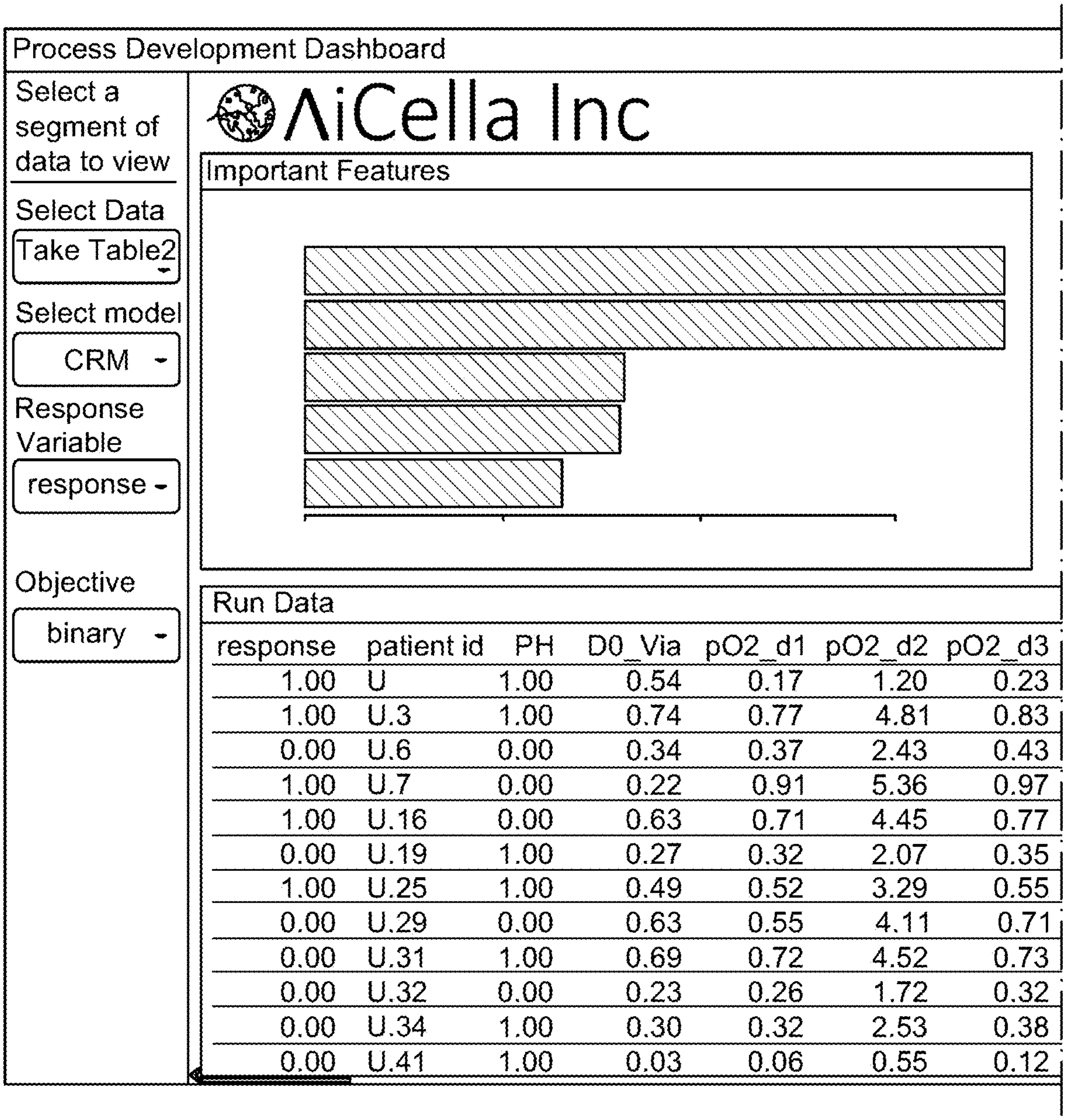
FIG. 6A is an illustration of a graphical user interface in accordance with some embodiments of the present disclosure.
Figure 6A:
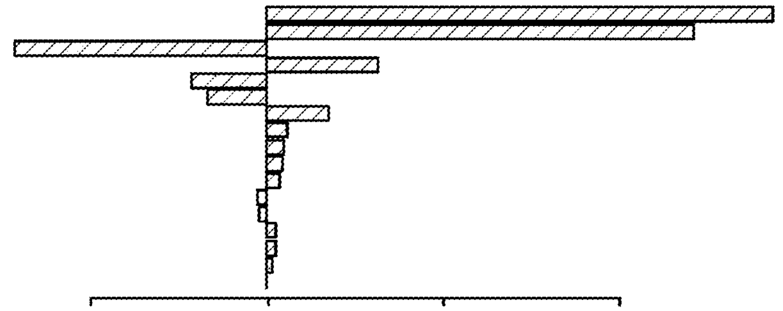
Figure 6A:
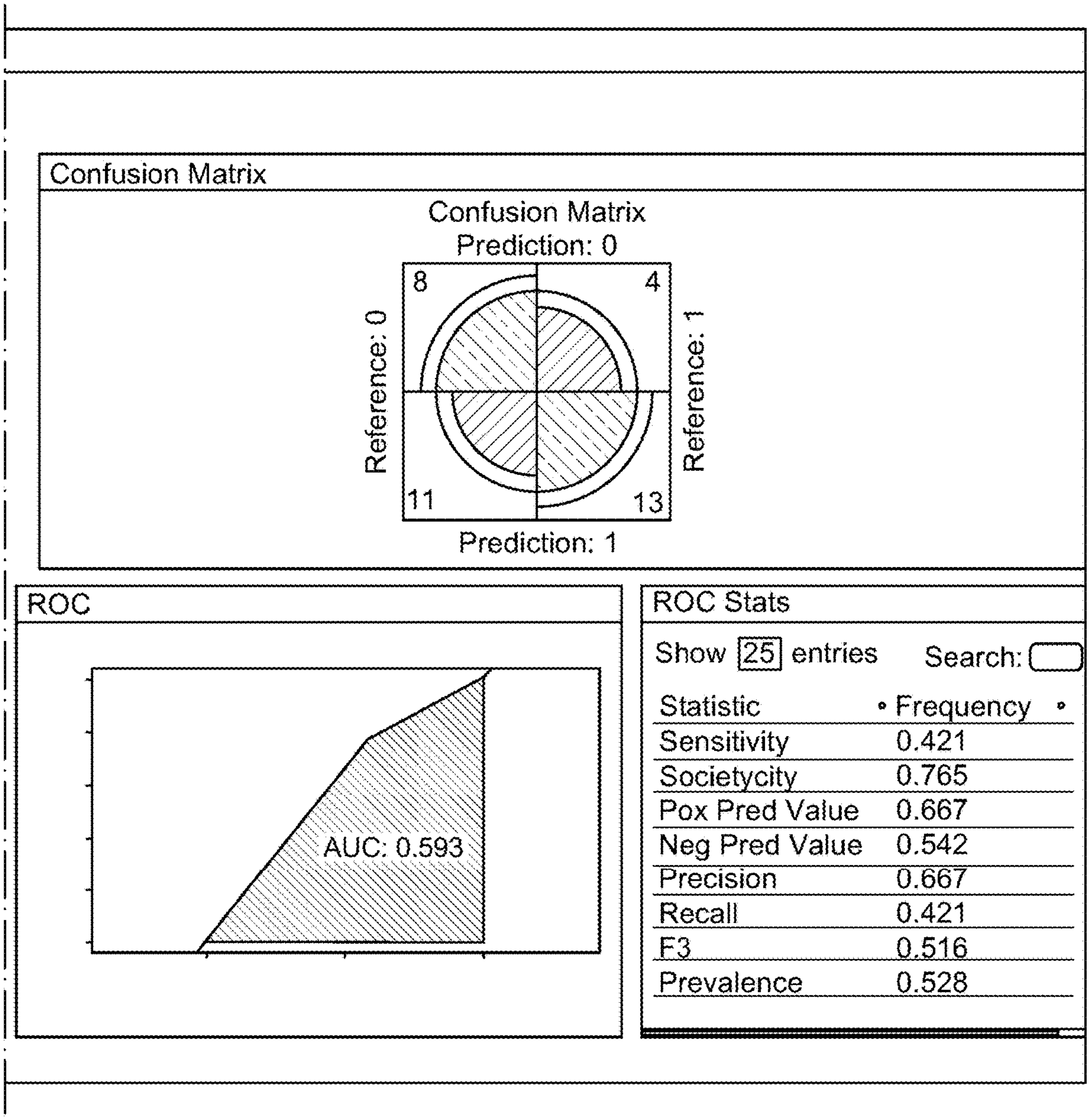

FIG. 6A illustrates a graphical user interface including a visualization tool built in accordance with some embodiments of the present disclosure. As illustrated in FIG. 6A, the visualization tool can load data from a database including real process development data paired with clinical outcomes. For example, this file includes a binary "response" variable that indicates clinical outcomes (i.e., response or no response). The real process development data can be analyzed by a trained machine learning model, for example LightGBM. The results of the analysis are displayed in the graphical user interface. For example, the results or output of the trained algorithm indicates the five most important factors measured in the process impacting clinical response are shown above. In the illustrated example, the most important factors impacting clinical response include the viability on day 0, dissolved O2 on day 4, and the pH on day 3 of culture. The underlying sensitivity and specificity of the artificial intelligence model are also displayed. As shown, the model had significant sensitivity and specificity to detect treatment response at of the model at 83.3% and 92.9%, respectively.

In some embodiments, the graphical user interface forms a web application, a desktop application, a smart phone application or the like. The graphical user interface can include a plurality of dropdown windows or menus allowing for a user to select between data that they want analyzed, the trained algorithms the user wants to use to analyze the data, and the response variable the user interested in and the like.

Figure 6B:
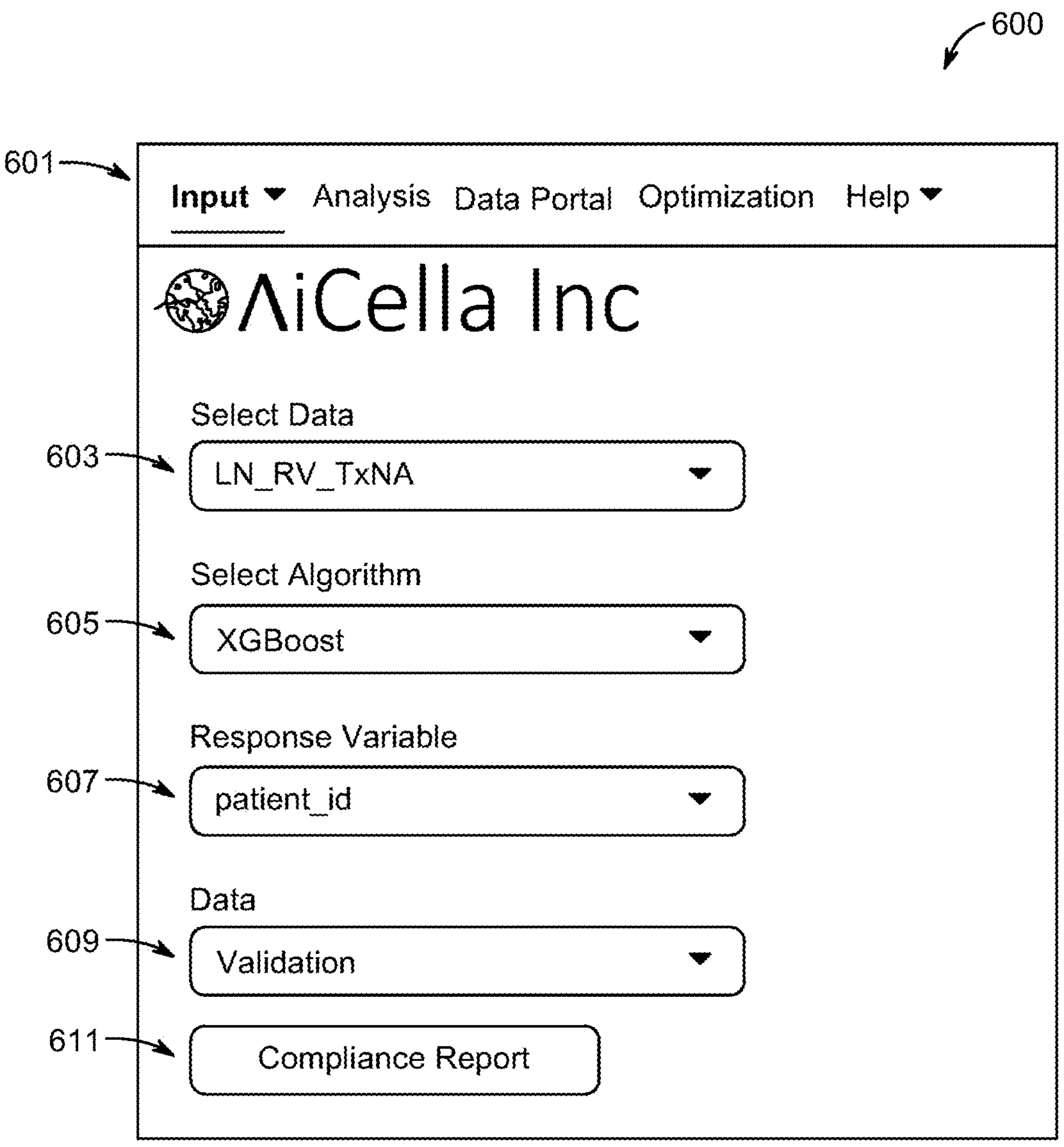
FIG. 6B is an illustration of a graphical user interface in accordance with some embodiments of the present disclosure.

As illustrated in FIG. 6B, a graphical user interface 600 can include a first landing page, an input page 601, where a user is able to select a dataset 603, select an algorithm 605, a response variable 607 and a data field 609. In addition, by selecting the "Compliance Report" action button 611, users can generate a data file. In some embodiments, the data file can be further presented in a printable format suitable for discussions with government regulators.

Figure 6C:
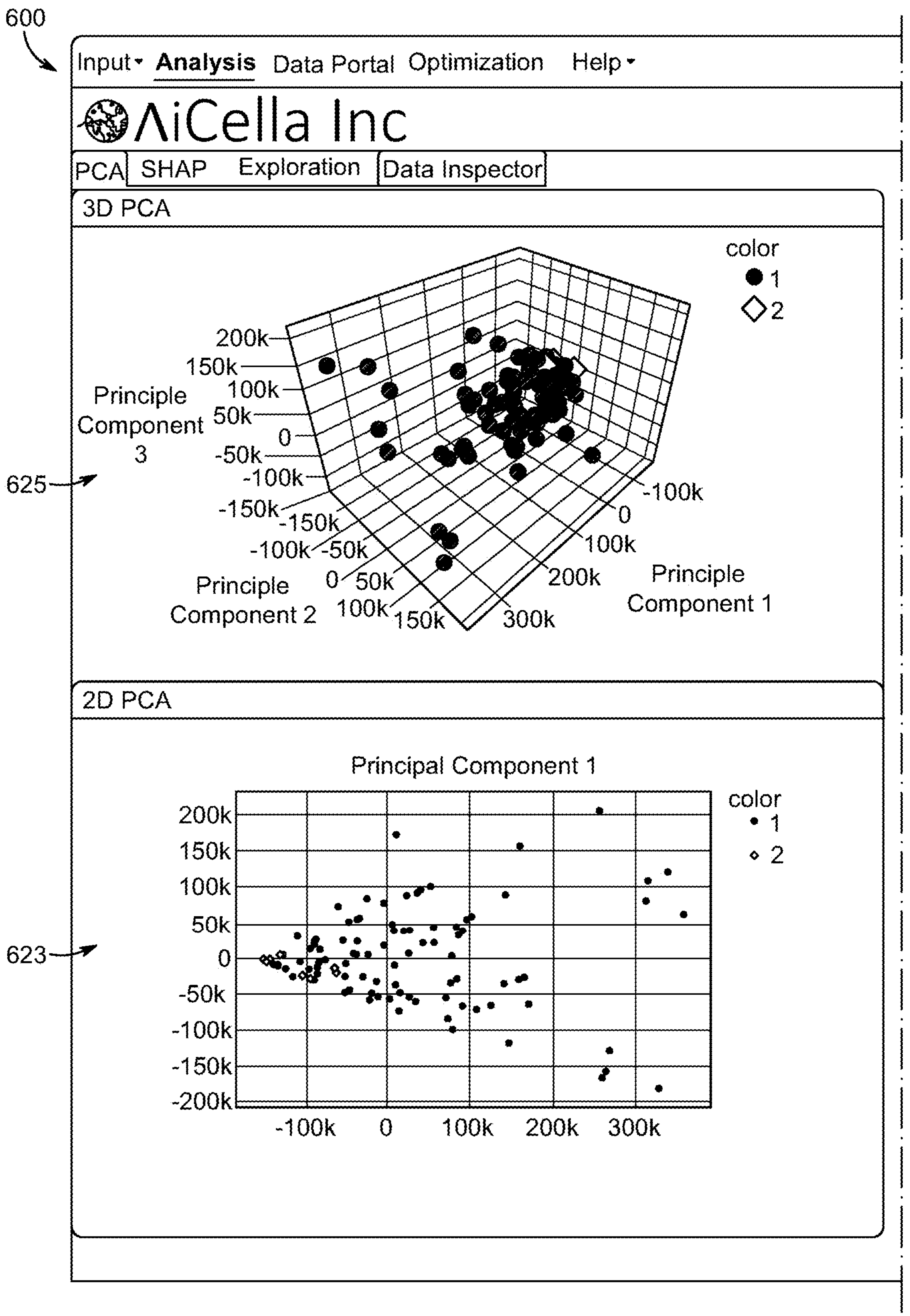
FIG. 6C is an illustration of a graphical user interface in accordance with some embodiments of the present disclosure.
Figure 6C:
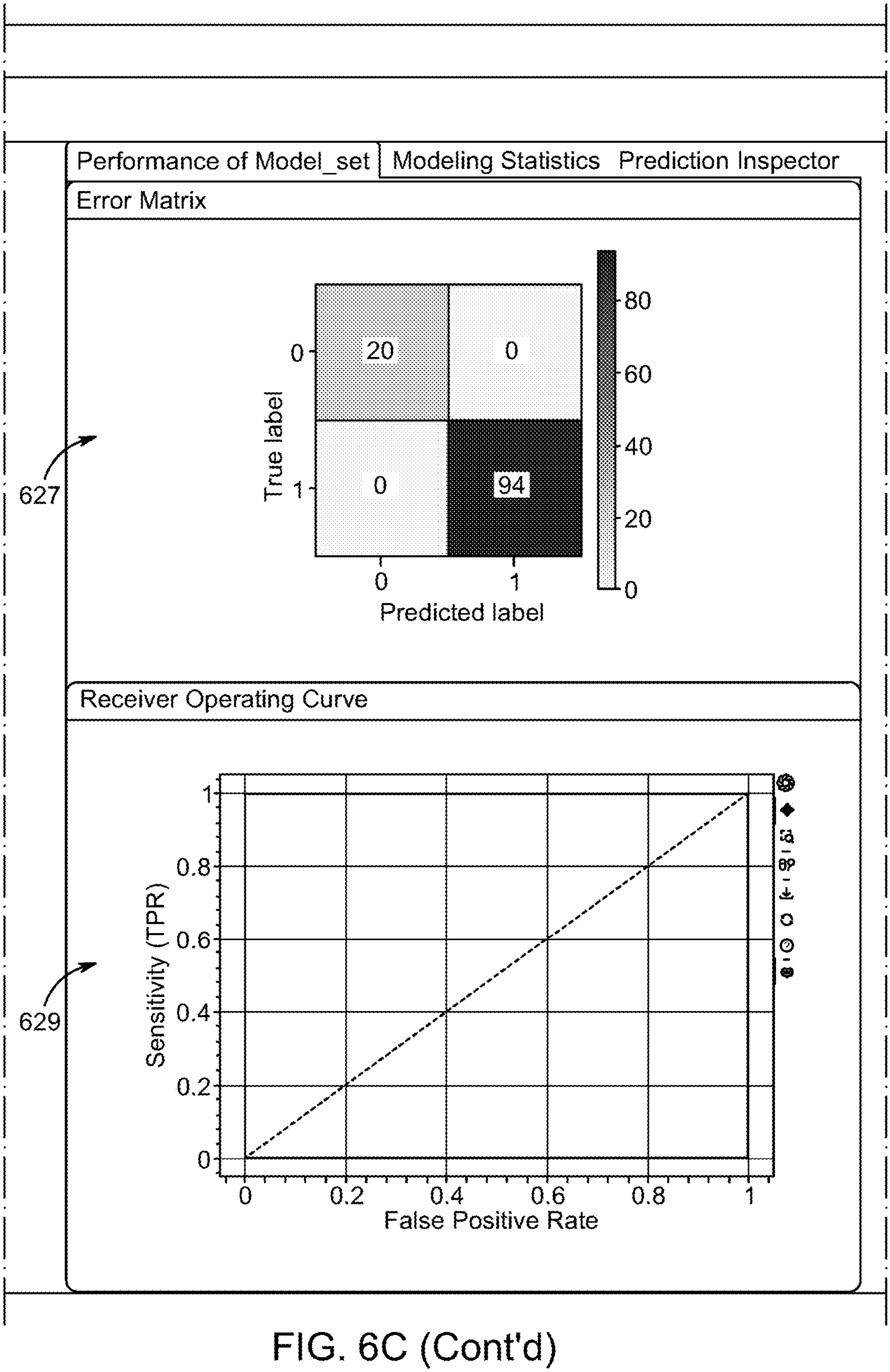
Figure 6C:
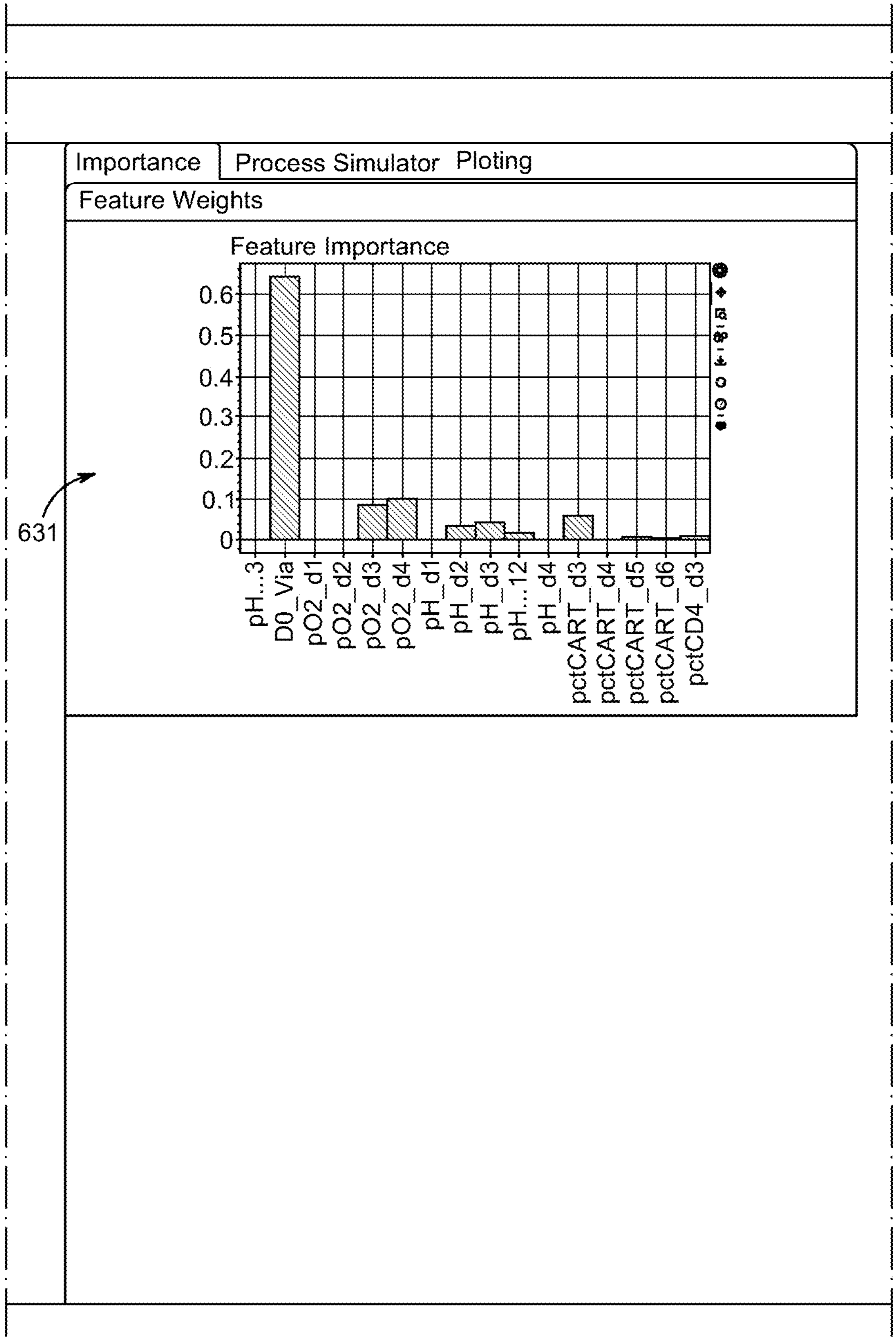
Figure 6C:
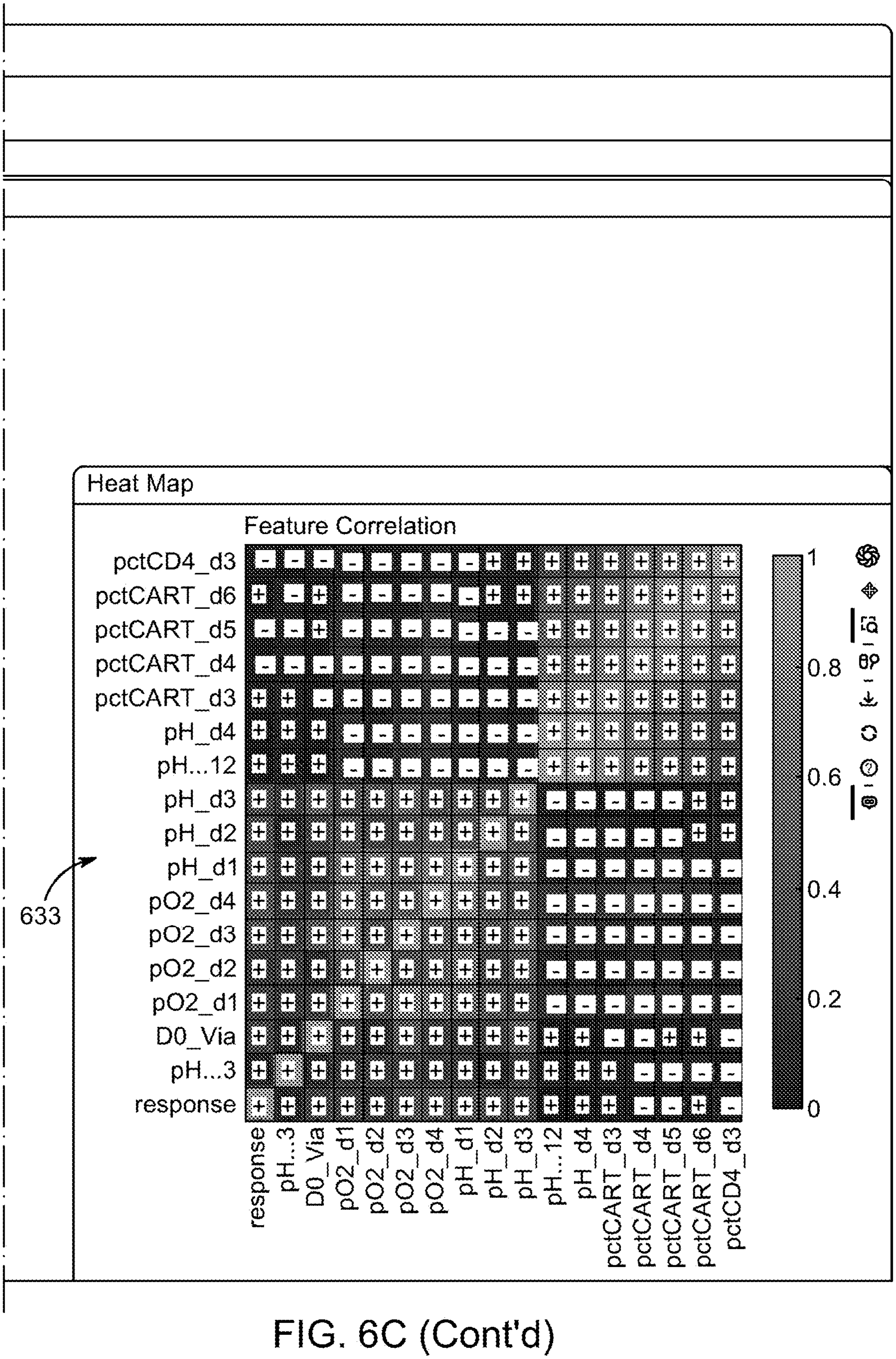

As illustrated in FIG. 6C, an analysis portion 621 of the graphical user interface 600 can include charts of two-dimensional 623 and three-dimensional 625 principal components analysis, indicating the features most relevant to the analysis. The analysis portion 621 can include an error matrix 627 indicating true positives, which are cases where the model correctly predicts the positive class; true negatives, which are the cases where the model correctly predicts the negative class; false positives, which are cases where the model incorrectly predicts the positive class; and false negatives, which are the cases where the model incorrectly predicts the negative class.

The receiver operating curve (ROC) 629 graphically illustrates the model performance in terms of specificity and sensitivity. Part of the ROC, the measurement of the AUC (area under the curve) is a metric that indicates the model performance. Numbers closer to 0.5 indicate the prediction is close to a coin flip, i.e., 50/50. Features important to each model can be illustrated by a features weight chart 631 and a heat map 633.

Figure 6D:
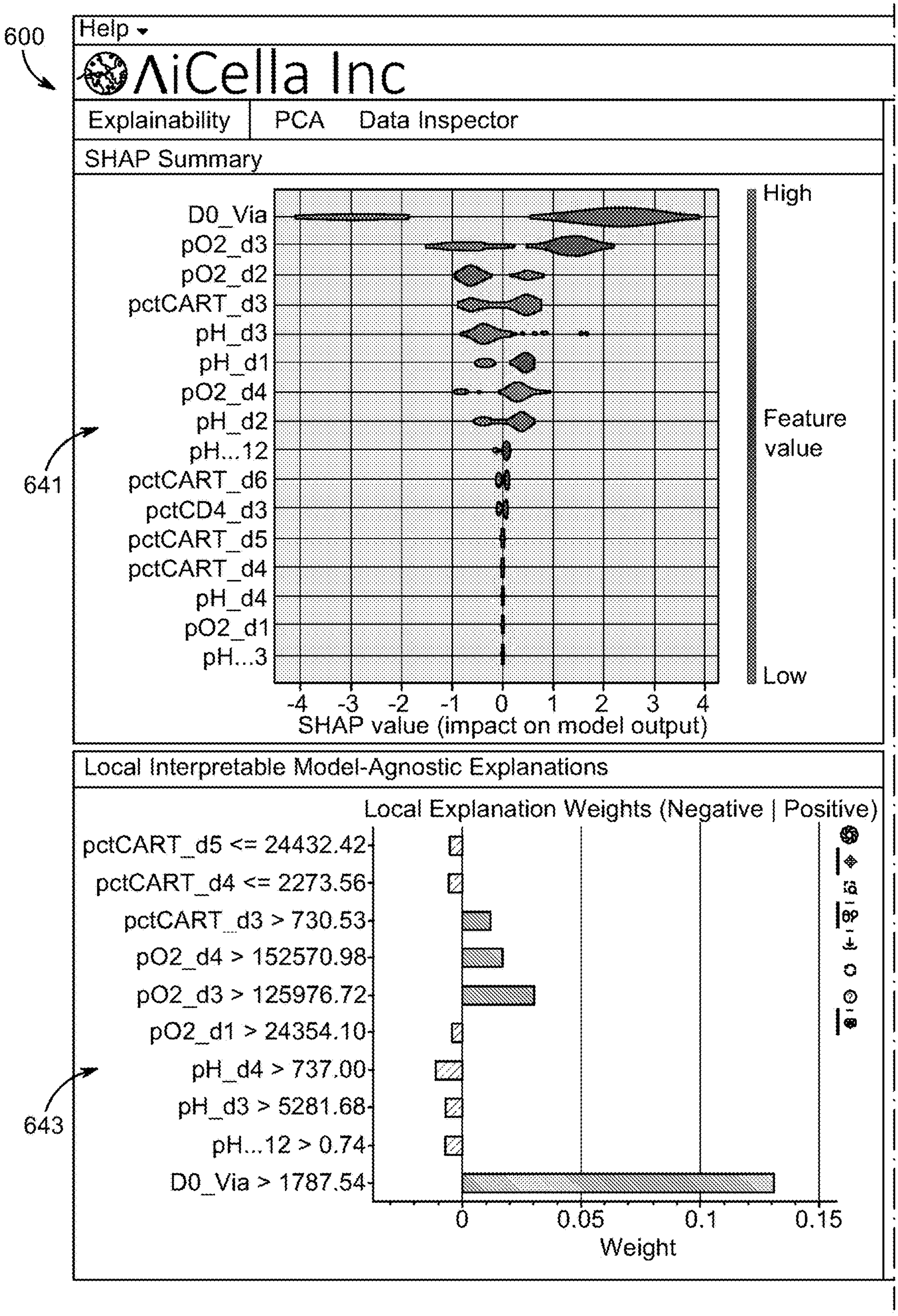
FIG. 6D is an illustration of a graphical user interface in accordance with some embodiments of the present disclosure.
Figure 6D:
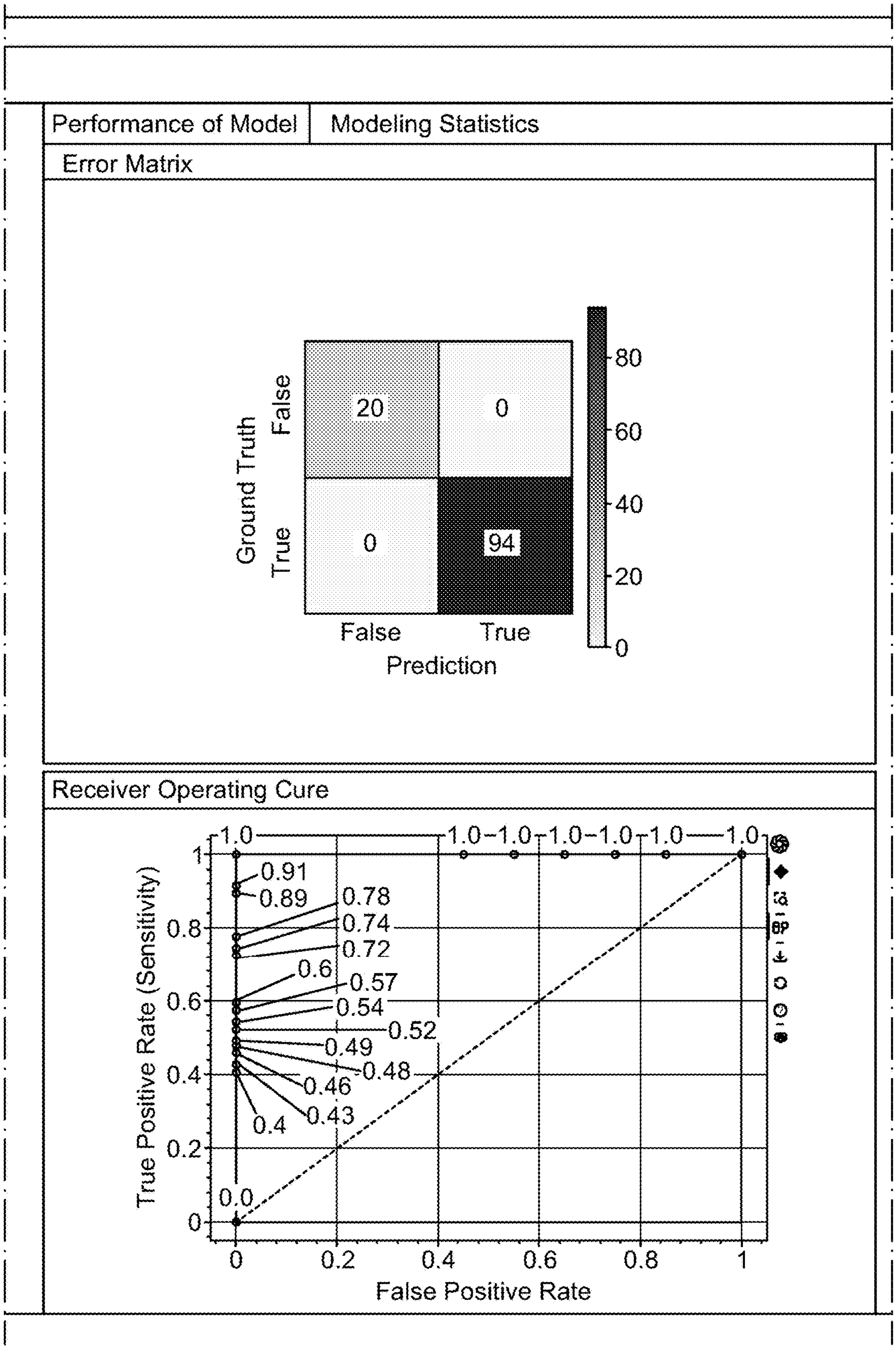
Figure 6D:
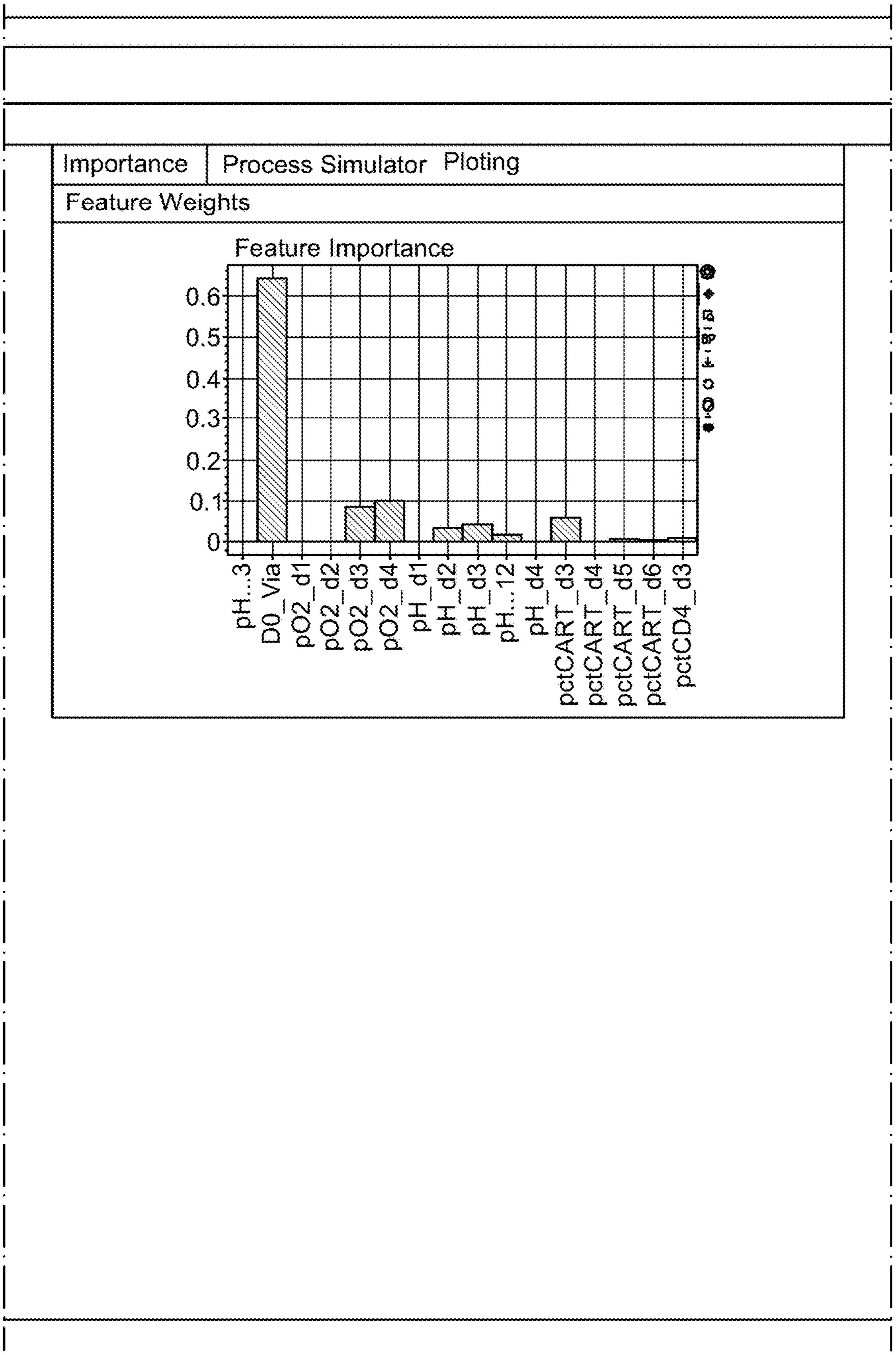
Figure 6D:
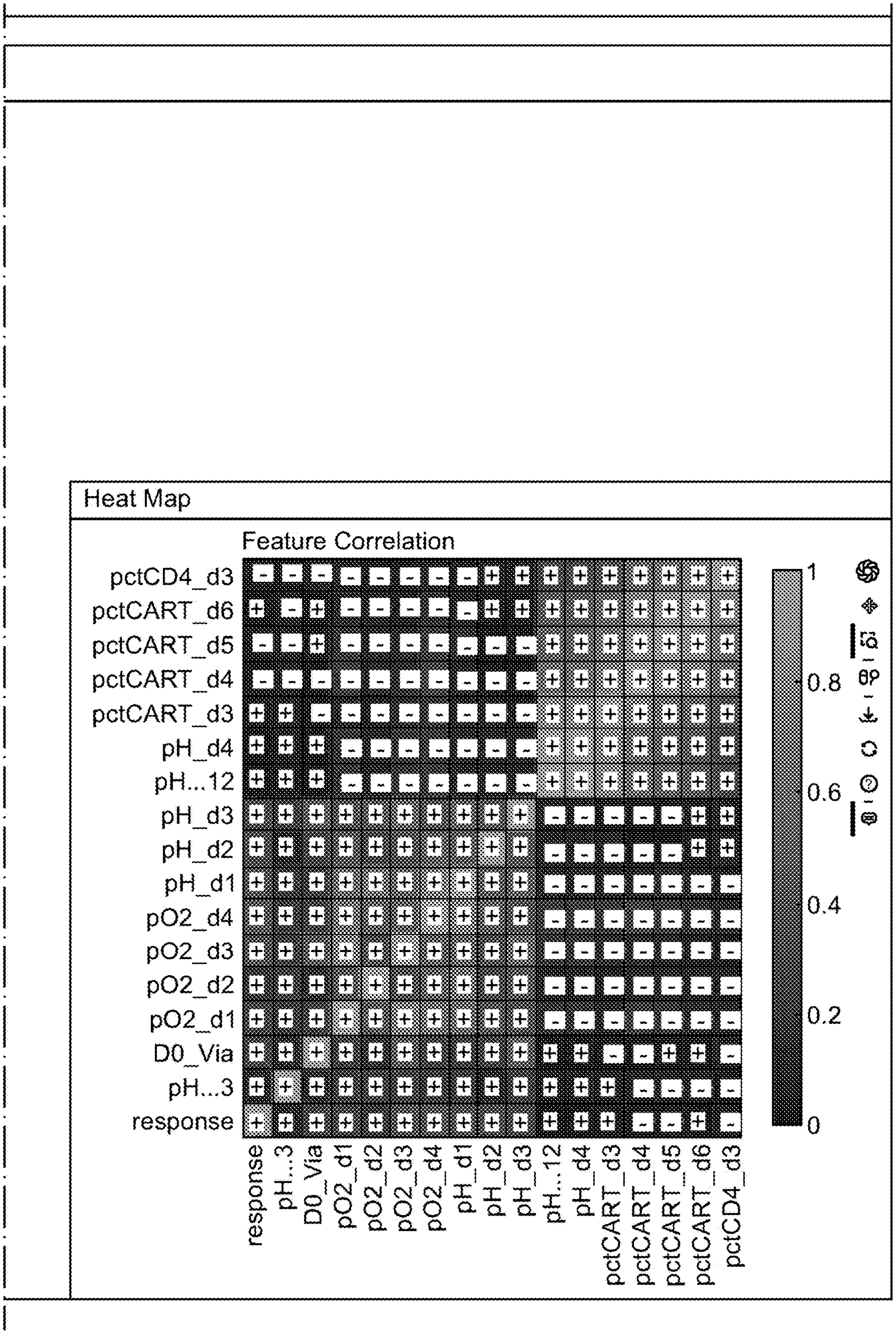

As shown in FIG. 6D, the analysis or explainability portion of the graphical user interface 600 can also include sections to provide explainability of machine learning processes such as a SHAP summary 641 or a SHAP 643 plot which can illustrate how each feature impacts the model prediction, output and/or performance. SHAP values assign an importance value to each feature in a model. Features with positive SHAP values positively impact the prediction, while those with negative values have a negative impact, and the magnitude is a reflection of the strength of the effect. The explainability tab can also include local interpretable model agnostic explanations 643.

Figure 6E:
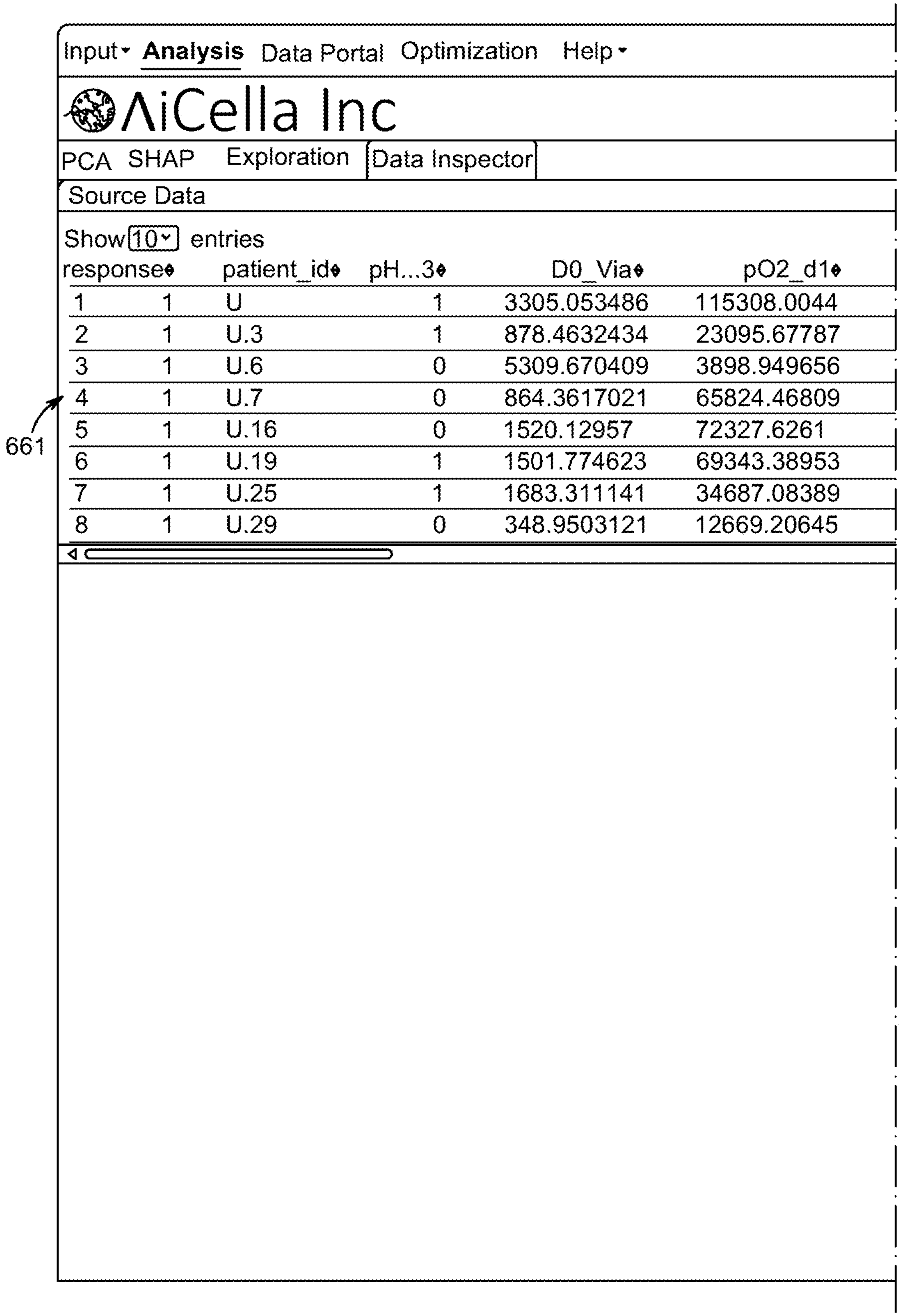
FIG. 6E is an illustration of a graphical user interface in accordance with some embodiments of the present disclosure.
Figure 6E:
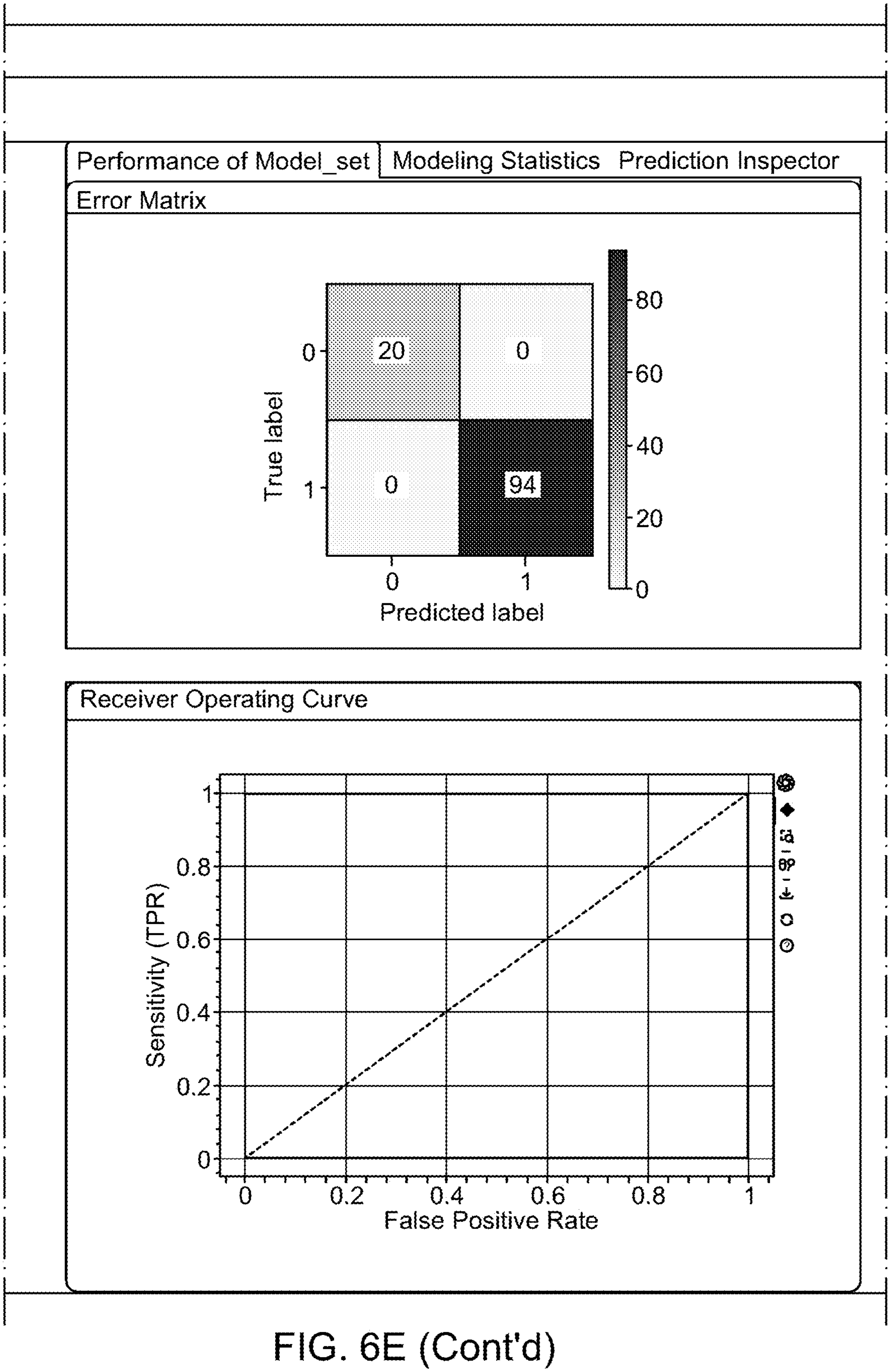
Figure 6E:
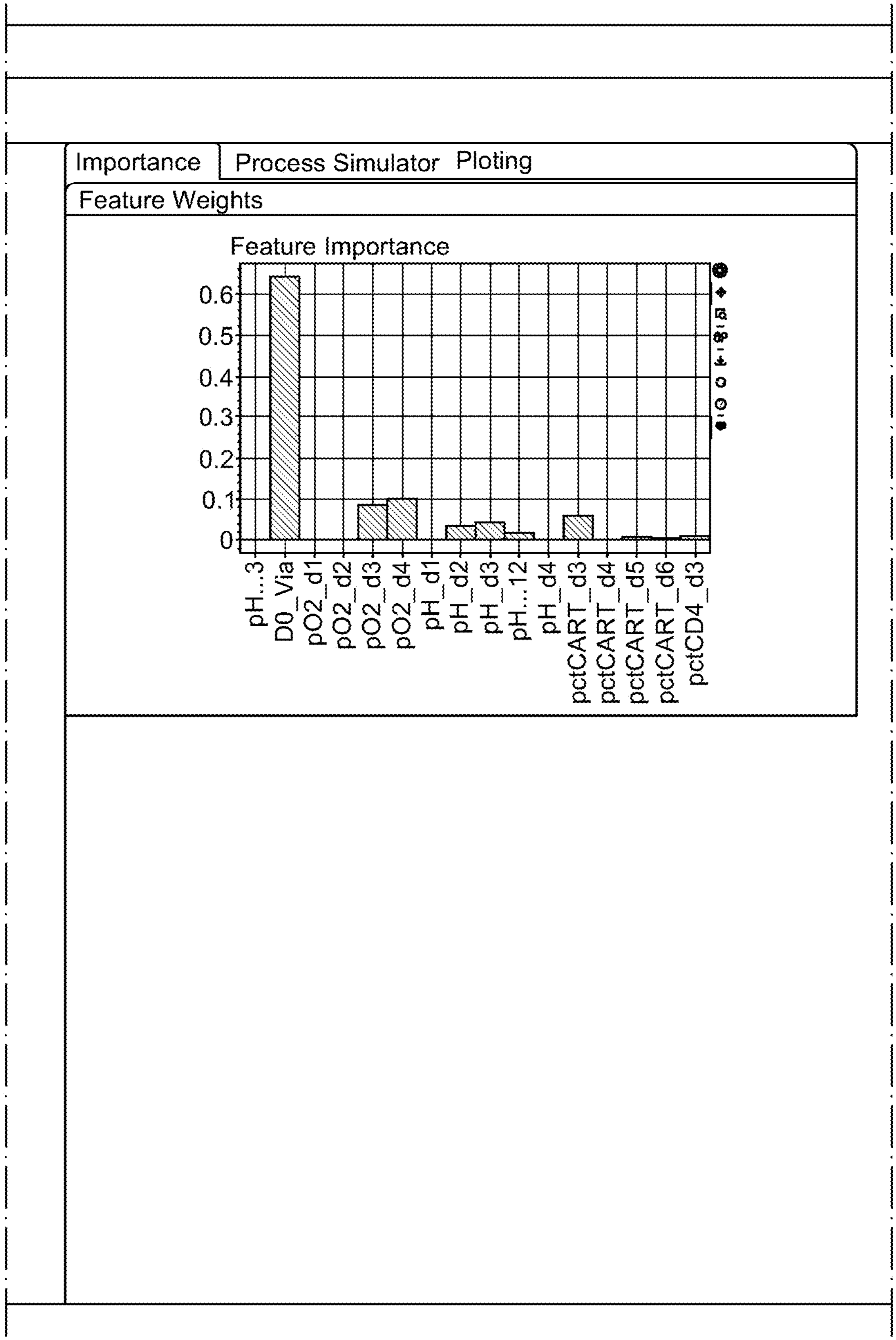
Figure 6E:
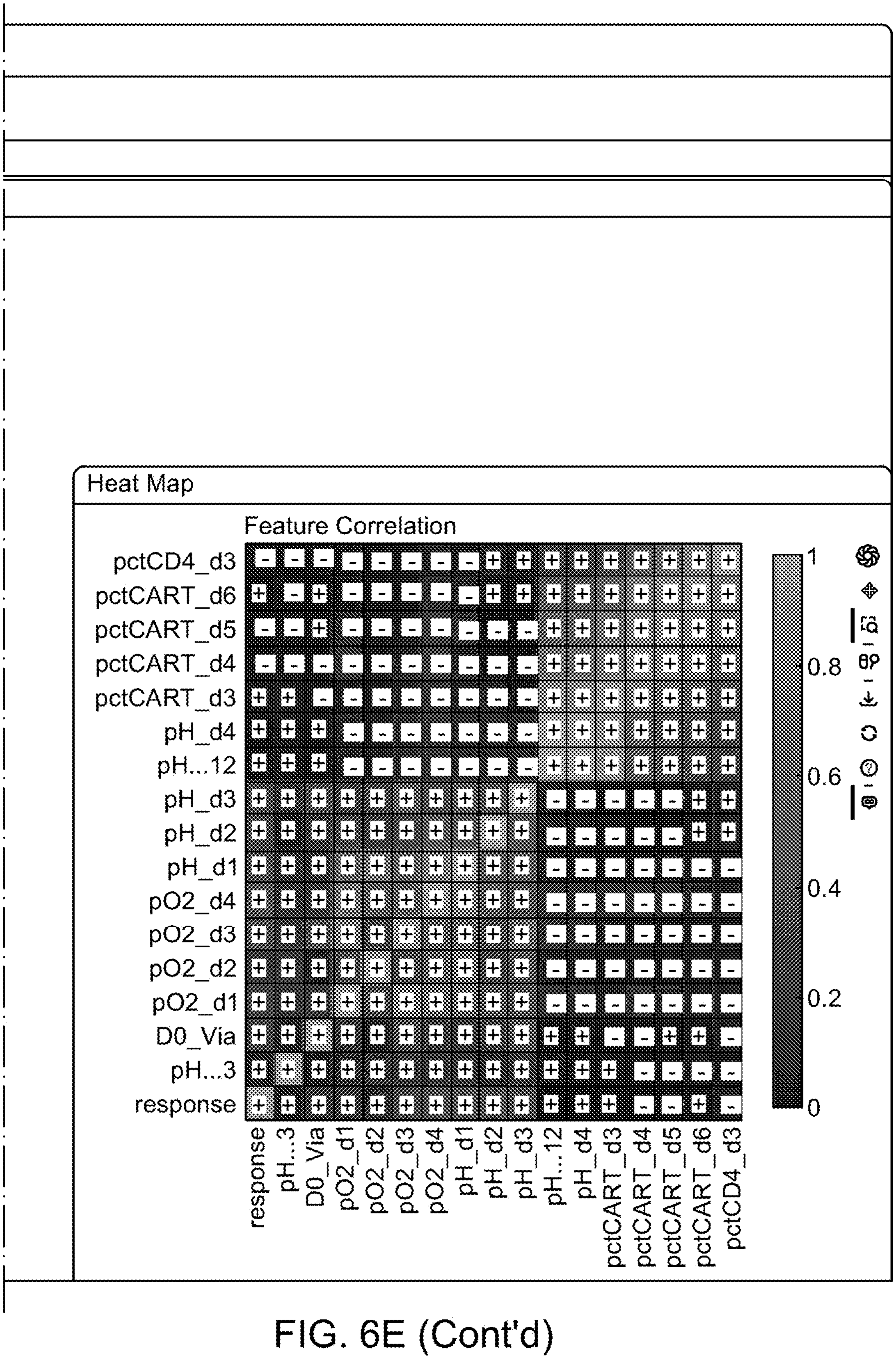

FIG. 6E illustrates that the graphical user interface 600 includes a data inspector 661 that includes the original data file that was submitted for analysis using machine learning. By allowing for a comparison or an inspection of the original data file, a user or automated process can confirm that the data transfer to the SQL database did not result in loss or corruption.

Figure 6F:
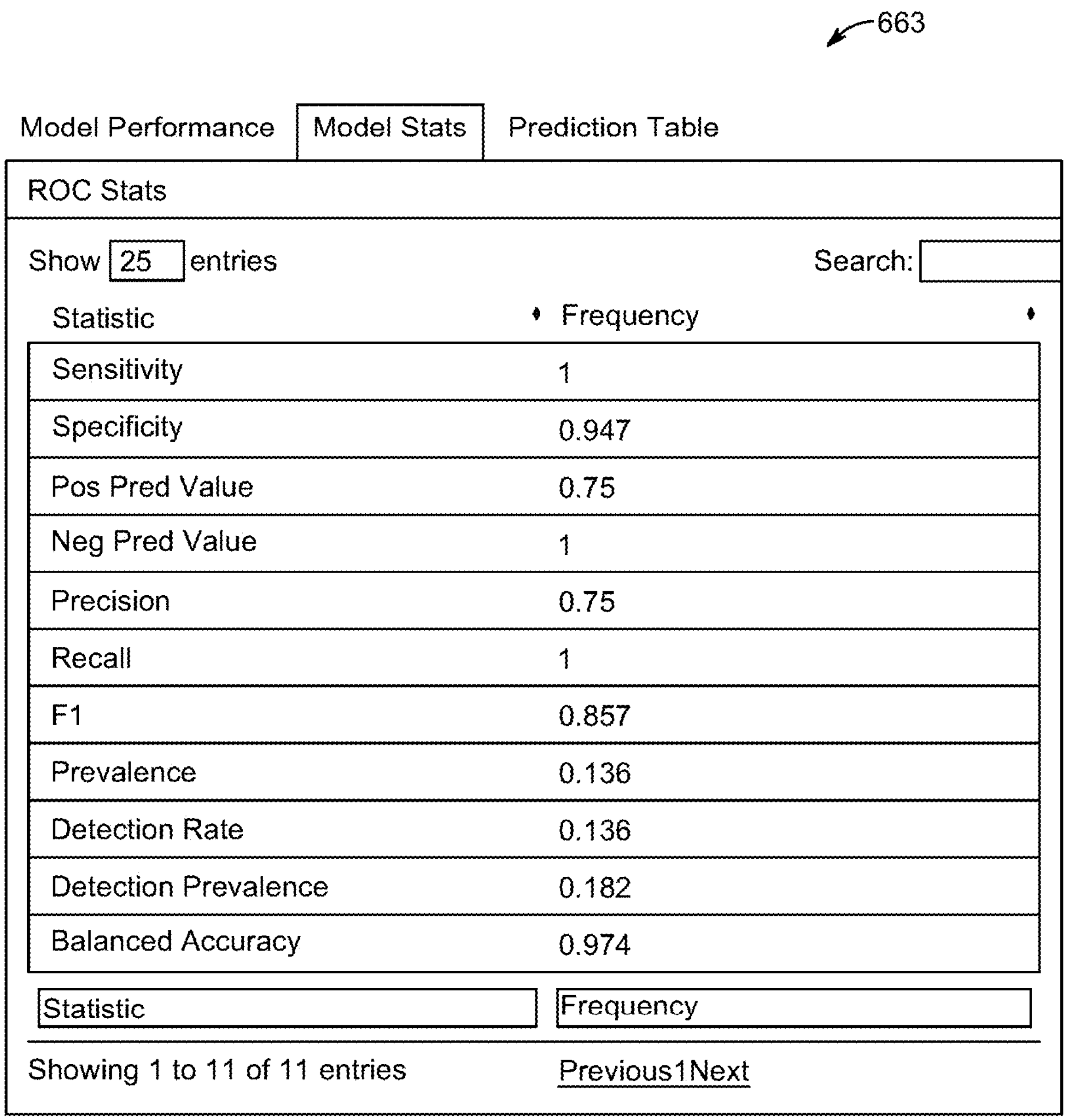
FIG. 6F is an illustration of a graphical user interface in accordance with some embodiments of the present disclosure.

FIG. 6F illustrates that the graphical user interface 600 can include modeling statistics 663. For example, statistics indicating model performance can be provided to a user. These statistics can include sensitivity, specificity, positive prediction value, negative prediction value, precision, recall, F1, prevalence, detection rate, detection prevalence, balanced accuracy, and the like.

As shown in FIG. 6G, the graphical user interface 600 can include a prediction inspector 665. The prediction inspector provides predictions for patients. The illustrated example represents the predicted probability for each individual patient as calculated by the XGBoost algorithm.

Figure 6H:
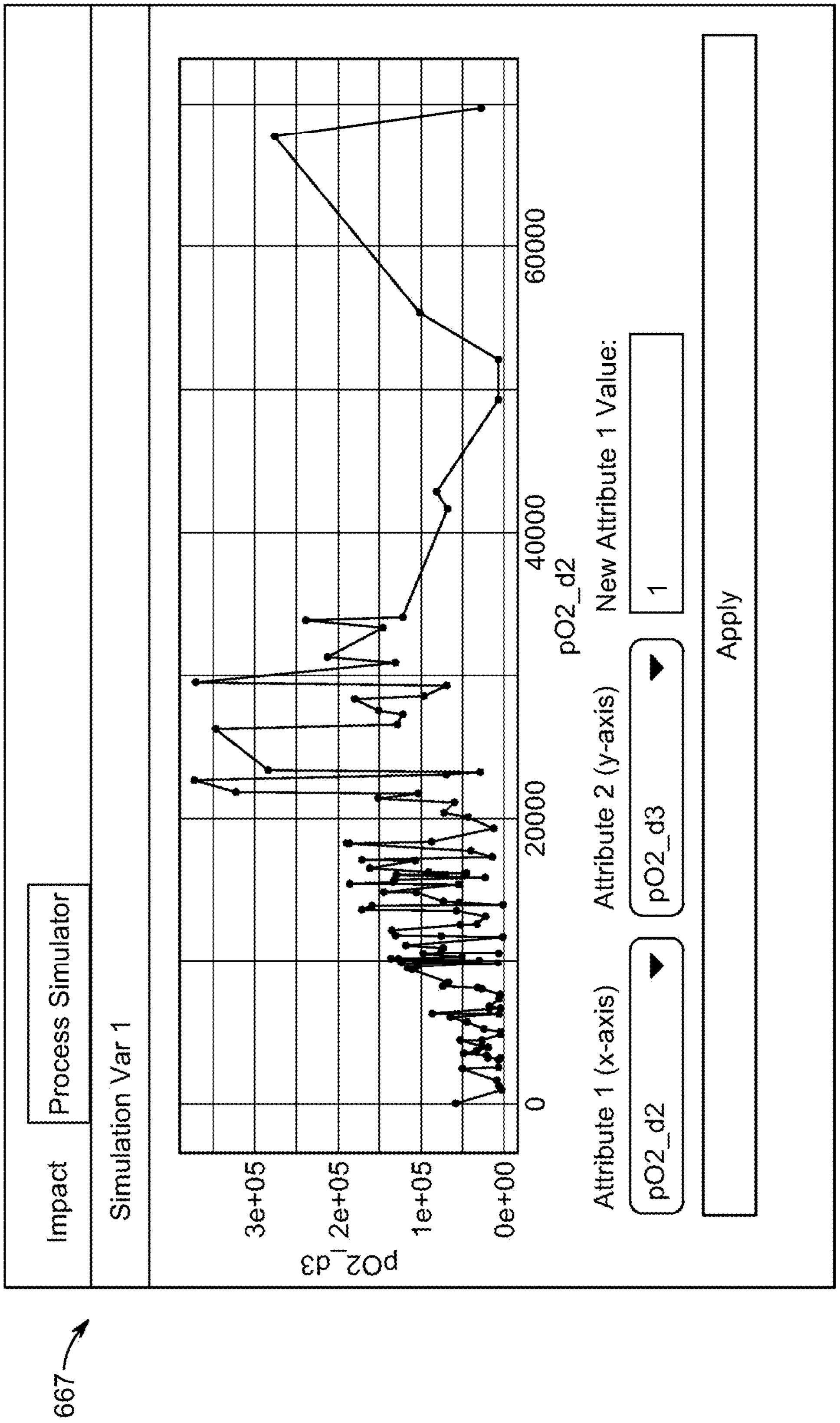
FIG. 6H is an illustration of a graphical user interface in accordance with some embodiments of the present disclosure.

FIG. 6H illustrates that the graphical user interface 600 includes a process simulator 667. The process simulator can demonstrate how one or more attributes can change performance. The process simulator can allow a user to input a different attribute value and simulate performance for the process engineering platform based on the attribute value. Any parameter that is measured and included in the dataset can be plotted and modified by the user. A user may provide input via the graphical user interface to interact with the provided data. For example, a user can make a change to a parameter value by picking a point in the plot and pressing the "Apply" button. Once the change is applied, the machine learning algorithm can be re-run with the new value, and the impact is reflected in the dashboard graphs. In some embodiments, the original value and the simulation value can be visualized at the same time. Any of the parameters displayed in the graphical user interface can be changed, which can then be used to update the machine learning algorithm, and then generate resulting output that can be replotted across the entire dashboard. In some embodiments, the simulation outputs are determined by rerunning the algorithm after selecting and changing the input value on the graph in the "Process Simulator" tab and pressing the "Apply" button.

Figure 6I:
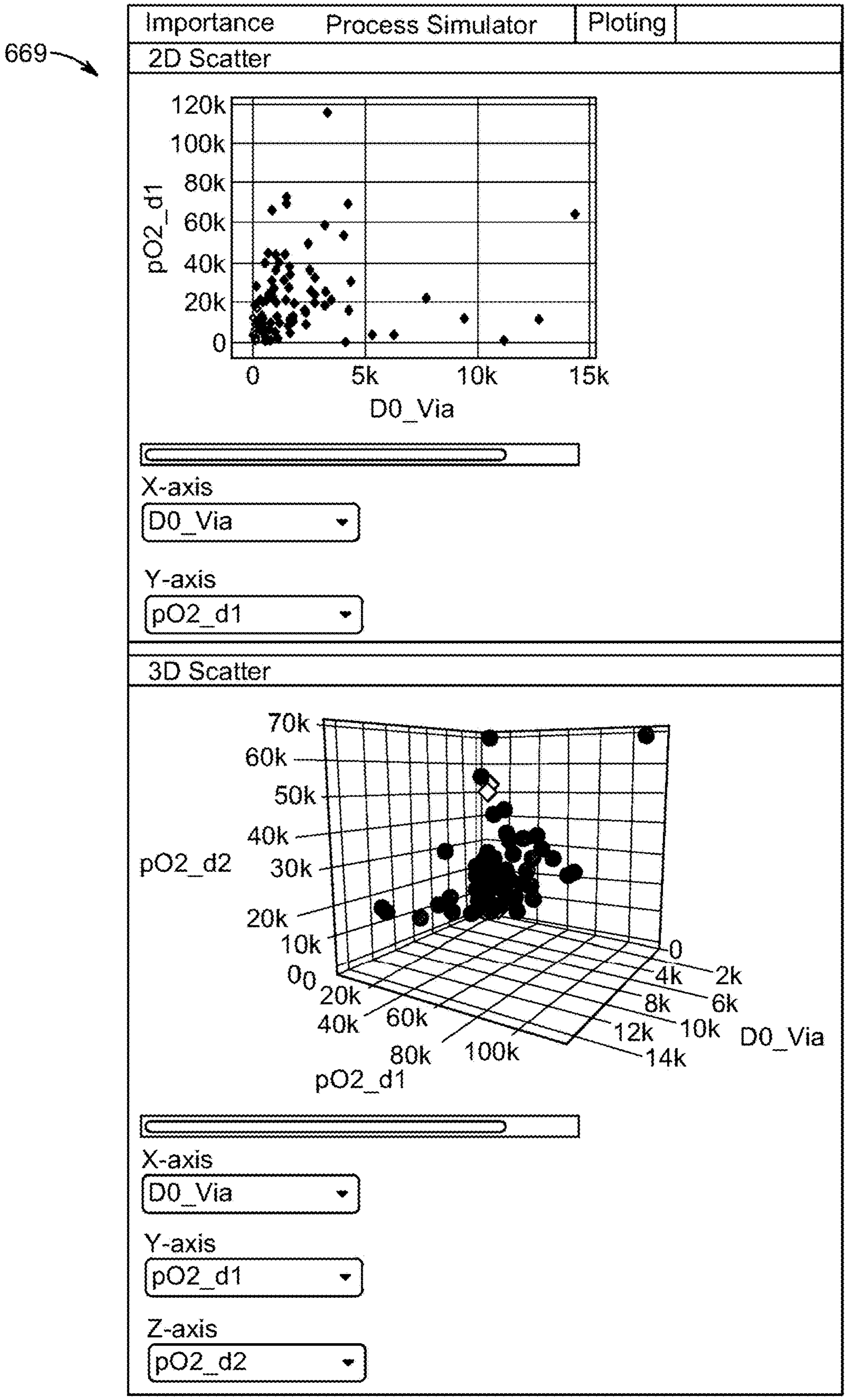
FIG. 6I is an illustration of a graphical user interface in accordance with some embodiments of the present disclosure.

FIG. 6I illustrates that the graphical user interface 600 includes plotting tabs 669. Plotting tabs can be used to visualize trends in data. One or more trends of interest, such as oxygen delivery (dO2), pH, CAR-T expression, and the like can be plotted in "Process Simulator" tab to give users insights into correlative relationships between different parameters of interest. Any parameter displayed in the graphical user interface can be trended.

The graphical user interface 600 can illustrate the performance of one or more machine learning models trained in accordance with the systems and methods described herein. For example, performance of a plurality of models can be illustrated within the graphical user interface. In some embodiments, performance of nine separate machine learning models including a logistic regression model, elastic net, k-nearest neighbor, decision tree, random forest, support vector machine, light gradient boosting machine classifier, extreme gradient boosting classifier, or multi-layer perceptron are used. Performance can be characterized in terms of accuracy and the area under the curve for a receiver operating characteristic (ROC AUC).

In the illustrated example, the logistic regression model may utilize a simple logistic regression with [L1, L2] penalty, [liblinear, saga] solver, and inverse regularization strength C=[1.0, 0.9, 0.7]. The illustrated logistic regression model includes an accuracy of 0.89 and a ROC AUC of 0.81.

In the illustrated example, the elastic Net model utilizes a more complex version of the Logistic Regression which mixes the L1 and L2 penalty with a balance ratio, with [Elastic Net] penalty, [SAGA] solver, inverse regularization strength C=[1.0, 0.9. 0.7], and L1 to L2 mixing ratio=[0.7, 0.5, 0.2]. The illustrated elastic net model has an accuracy of 0.91, and a ROC AUC: 0.95.

The illustrated example also includes a k-nearest neighbor model with n_neighbors=[5, 20, 10], and results in an accuracy of 0.87 and a ROC AUC: 0.93.

The illustrated example also includes a decision tree with [Gini Impurity] loss function, max depth=[None, 12, 121], minimum sample split=[2, 5, 7], max leaf nodes=[None, 128, 500]. The decision tree has an accuracy of 0.91, and ROC AUC: 0.91.

The illustrated example also includes a random Forest classifier with [Gini Impurity] loss function for trees, number of trees=[100, 128, 200, 500, 700], max depth=[None, 12, 121], minimum sample split=[2, 5, 7], and max leaf nodes=[None, 128, 500]. The resulting model has an accuracy of 0.96, and a ROC AUC: 1.0.

The illustrated example also includes a Support Vector Machine Classifier with [RBF] kernel, and Inverse Regularization Strength C=[1.0, 0.9, 0.7]. The model includes an accuracy of 0.85, and ROC AUC: 0.96.

The illustrated example also includes a Light GBM, or a Light Gradient Boosting Machine Classifier trained for [6, 12, 50] rounds without early stopping or in model cross validation, with number of leaves=[12, 31, 50], and criteria set to optimized for binary error. The Light GBM has an accuracy of 0.92, and ROC AUC: 0.99.

The illustrated example also includes XGBoost, an Extreme Gradient Boosting Classifier with booster set to [dart, gbtree], tree max depth=[6, 12, 50], eta (learning rate)=[0.2, 0.5, 0.7], Lambda (L2 Regularization)=[1, 2, 12], Alpha (L1 Regularization)=[0, 0.7, 1.2]. The XGBoost model has an accuracy of 0.95, and ROC AUC: 0.98.

The illustrated example also includes a deep learning model, a Multi-Layer Perceptron Classifier, which is a neural network based classifier using fully connected network with the size of hidden layers set to [(121, 500, 200), (200, 500), (17, 121, 21)], Initial Learning Rate=[0.0001, 0.0007, 0.0012, 0.007, 0.012], Learning Rate Schedule=["Adaptive"], Activation Function=[ReLU], Optimizer=[Adam Optimizer], Batch Size=["auto", 16, 32], and Alpha (L2 Regularization Strength)=[0, 0.0001, 0.001]. The multilayer perceptron classifier had an accuracy of 0.93, with a ROC AUC: 0.86.

Figure 7:
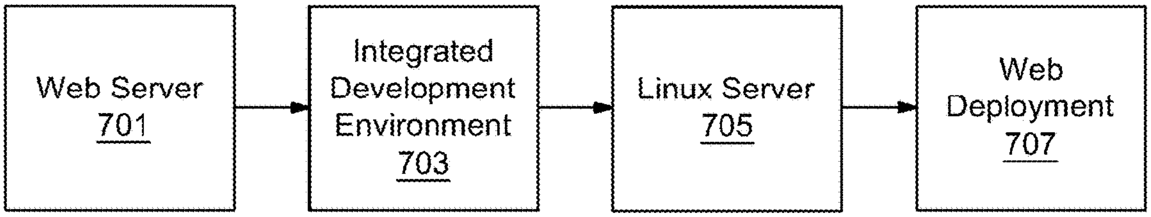
FIG. 7 is an illustration of computer system architecture in accordance with some embodiments of the present disclosure.

FIG. 7 provides a diagram showing an example system architecture. The system architecture can include a web server 701, integrated development environment 703, in communication with the linux server 705, and web deployment 707. The system architecture consists of structured data input stored in a SQL database, which is interfaced with the Posit Workbench (i.e. RStudio). The RStudio is the IDE used to code the AI/ML "engine" and well as the RShiny web interface. The code is published to the Linux server, which serves the Rshiny website via Posit Connect. The entire chain can utilize Amazon Web Services (AWS) for deployment.

Figure 8:
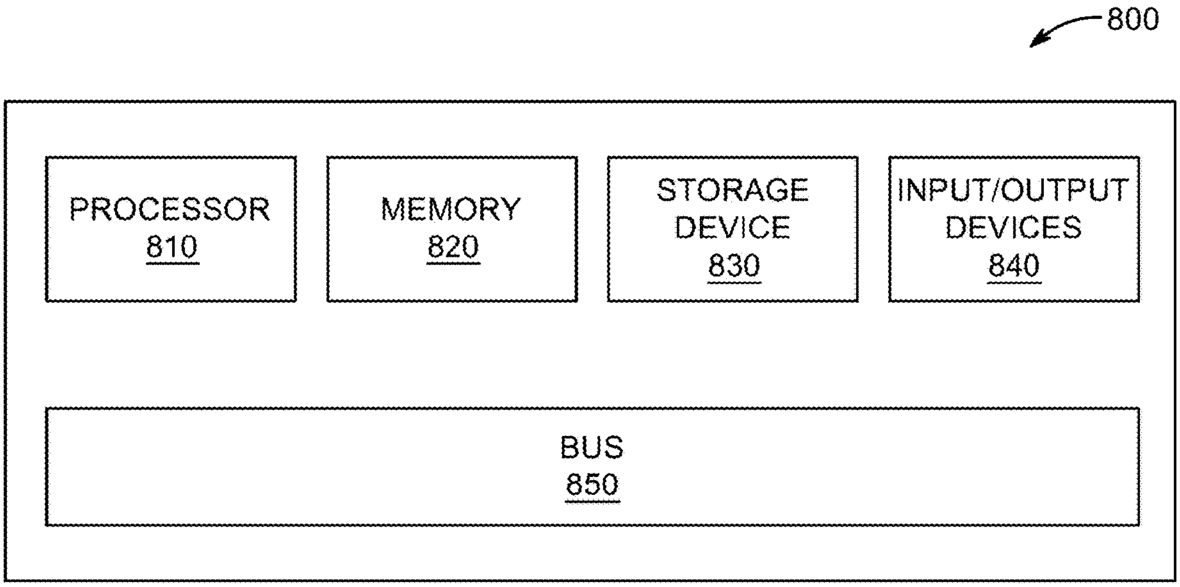
FIG. 8 is an illustration of computer system architecture in accordance with some embodiments of the present disclosure.

FIG. 8 depicts a block diagram illustrating an example of a computing system 800 consistent with implementations of the current subject matter. Referring to FIGS. 1-7, the computing system 800 can be used to implement any components therein.

As shown in FIG. 8, the computing system 800 can include a processor 810, a memory 820, a storage device 830, and an input/output device 840. The processor 810, the memory 820, the storage device 830, and the input/output device 840 can be interconnected via a system bus 850. The processor 810 is capable of processing instructions for execution within the computing system 800. Such executed instructions can implement one or more components of, for example, the machine learning models described herein. In some example embodiments, the processor 810 can be a single-threaded processor. Alternately, the processor 810 can be a multi-threaded processor.

The processor 810 is capable of processing instructions stored in the memory 820 and/or on the storage device 830 to display graphical information for a user interface provided via the input/output device 840.

The memory 820 is a computer readable medium such as volatile or non-volatile that stores information within the computing system 800. The memory 820 can store data structures representing configuration object databases, for example. The storage device 830 is capable of providing persistent storage for the computing system 800. The storage device 830 can be a solid state drive, a floppy disk device, a hard disk device, an optical disk device, or a tape device, or other suitable persistent storage means. The input/output device 840 provides input/output operations for the computing system 800. In some example embodiments, the input/output device 840 includes a keyboard and/or pointing device. In various implementations, the input/output device 840 includes a display unit for displaying graphical user interfaces.

According to some example embodiments, the input/output device 840 can provide input/output operations for a network device. For example, the input/output device 840 can include Ethernet ports or other networking ports to communicate with one or more wired and/or wireless networks (e.g., a local area network (LAN), a wide area network (WAN), the Internet).

In some example embodiments, the computing system 800 can be used to execute various interactive computer software applications that can be used for organization, analysis and/or storage of data in various formats. Alternatively, the computing system 800 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 840. The user interface can be generated and presented to a user by the computing system 800 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random query memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, recurrent provided to the user can be any form of sensory recurrent, such as for example visual recurrent, auditory recurrent, or tactile recurrent; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

Systems, methods, and articles of manufacture, including computer program products, are provided for machine learning enabled prediction of process parameters most relevant for the engineering of cells such as T-cells. Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer based methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc. Such computer systems may or may not rely on cloud-based architectures.

In the descriptions above and in the claims, phrases such as “at least one of” or “one or more of” may occur followed by a conjunctive list of elements or features. The term “and/or” may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases “at least one of A and B;” “one or more of A and B;” and “A and/or B” are each intended to mean “A alone, B alone, or A and B together.” A similar interpretation is also intended for lists including three or more items.

For example, the phrases “at least one of A, B, and C;” “one or more of A, B, and C;” and “A, B, and/or C” are each intended to mean “A alone, B alone, C alone, A and B together, A and C together, B and C together, or A and B and C together.” Use of the term “based on,” above and in the claims is intended to mean, “based at least in part on,” such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

I claim:

1. A simulation-assisted method for predicting a clinical response for a cell engineering process, the method comprising:

receiving, by at least one processor, a set of measured or recorded process parameters of the cell engineering process;

training a machine learning bioprocess simulation model on process parameter data and clinical response data to computationally replicate, in silico, time-dependent cell-population dynamics and product characteristics of the cell-engineering, wherein the process parameter data comprises:

operator identification, initial volume, donor, mixing, dilution speed, input bag rinsing, optical cell detection, product filling speed, waste extraction speed, intermediate volume, pre-wash cycles, pre-wash g-force, pre-wash sedimentation time, switch washing solution, lactate concentration, oxygen concentration, $CO_2$ concentration, hold time prior to freeze, cell freezing parameters, and thaw parameters;

executing by the at least one processor the machine learning bioprocess simulation model on the cell-engineering process;

generating, based on the simulation, a clinical response associated with the simulated biological outcome of the cell engineering process to produce a predicted clinical response;

generating, by the at least one processor, data usable to generate a visualization in a graphical user interface of the predicted clinical response; and implementing control logic that sets one or more process parameters in accordance with the predicted clinical response to regulate operation of the cell-engineering system.

2. The method of claim 1, wherein the machine learning model comprises at least one of logistic regression, an elastic net, a k-nearest neighbor, a decision tree, a random forest, a support vector machine, a support vector, a light gradient boosting method, an extreme gradient boosting method, a neural network, or a multi-layer perceptron.

3. The method of claim 1, wherein the machine learning model is further trained on in vitro assay results of the cell engineering process, wherein the in vitro assay results comprises one or more of a cell number, percentage phenotype, cell recovery data, cell diameter, hold time, expansion properties of the engineered cells, persistence properties of the engineered cells, cytokine release patterns, or cytotoxicity levels in vitro.

4. The method of claim 1, wherein the cell engineering process comprises a process for generating Chimeric Antigen Receptor (CAR) T cells.

5. The method of claim 1, further comprising pre-processing the received set of process parameters by at least one of cleaning, deduplicating, standardizing, transforming, applying feature engineering, normalizing, scaling, encoding, integrating, or reducing the received set of process parameters.

6. The method of claim 1, further comprising:

adjusting one or more process parameters of the cell engineering process based on the predicted clinical response.

7. The method of claim 1, further comprising:

generating a set of cells based on the cell engineering process having adjusted process parameters.

8. The method of claim 1, wherein providing the predicted clinical response further comprises:

displaying in a graphical user interface the predicted clinical response and at least one of: one or more characteristics of the trained machine learning model, or the received set of process parameters.

9. A method comprising:

obtaining a machine learning model which translates a set of process parameters of a cell engineering process into a simulated biological outcome;

training the machine learning model on process parameter data and clinical response data wherein the process parameter data comprises: operator identification, initial volume, donor, mixing, dilution speed, input bag rinsing, optical cell detection, product filling speed, waste extraction speed, intermediate volume, pre-wash cycles, pre-wash g-force, pre-wash sedimentation time, switch washing solution, lactate concentration, oxygen concentration, CO2 concentration, hold time prior to freeze, cell freezing parameters, and thaw parameters;

obtaining the set of process parameters characterizing the cell engineering process;

converting, using the machine learning model, handwritten process parameters to a structured dataset for computational analysis with the machine learning model;

applying the machine learning model in silico to the dataset to simulate a biological outcome of the cell-engineering process;

predicting using the trained machine learning model, a clinical response associated with the simulated biological outcome; and outputting or displaying, by the at least one processor, the predicted clinical response for use in adjusting or verifying process parameters of the cell-engineering process.

* * * * *